United States Patent [19]
Hassett et al.

[11] Patent Number: 6,090,084
[45] Date of Patent: *Jul. 18, 2000

[54] SHAPED GUIDING INTRODUCERS FOR USE WITH A CATHETER FOR THE TREATMENT OF ATRIAL ARRHYTHMIA

[75] Inventors: James A. Hassett; John D. Ockuly, both of Minnetonka, Minn.; John F. Swartz, Tulsa, Okla.

[73] Assignee: Daig Corporation, Minnetonka, Minn.

[*] Notice: This patent is subject to a terminal disclaimer.

[21] Appl. No.: 09/018,812

[22] Filed: Feb. 4, 1998

Related U.S. Application Data

[60] Continuation-in-part of application No. 08/949,929, Oct. 14, 1997, Pat. No. 5,902,289, which is a division of application No. 08/337,722, Nov. 14, 1994, Pat. No. 5,690,611, which is a continuation-in-part of application No. 08/272,014, Jul. 8, 1994, Pat. No. 5,575,766.

[51] Int. Cl.$^7$ .................................................. A61M 25/00
[52] U.S. Cl. ......................... 604/281; 604/280; 604/264; 128/772; 128/657
[58] Field of Search .................... 607/101, 15; 128/702, 128/705, 695, 772, 657; 604/49, 281, 510, 508, 500, 264, 280, 528, 532; 602/96, 115, 119

[56] References Cited

U.S. PATENT DOCUMENTS

| | | | |
|---|---|---|---|
| 5,497,774 | 3/1996 | Swartz et al. | 128/658 |
| 5,715,818 | 2/1998 | Swarts et al. | 128/642 |
| 5,725,512 | 3/1998 | Swartz et al. | 604/280 |
| 5,800,413 | 9/1998 | Swartz et al. | 604/280 |
| 5,846,223 | 12/1998 | Swartz et al. | 604/53 |
| 5,902,289 | 5/1999 | Swartz et al. | 604/281 |

*Primary Examiner*—John G. Weiss
*Assistant Examiner*—Dennis Ruhl
*Attorney, Agent, or Firm*—Scott R. Cox

[57] ABSTRACT

A process for the treatment of atrial arrhythmia by use of ablation and/or mapping procedures comprising ablating ablation tracks within the left and right atrium of the heart by use of precurved left and right atrium guiding introducers, including preferably a guiding introducer system for use in the left atrium comprising an inner and an outer guiding introducer. Also disclosed are shapes for the guiding introducers and the guiding introducer system to be used for the ablation and/or mapping of the discrete tracks within the left and right atrium.

21 Claims, 28 Drawing Sheets

RIGHT ATRIUM

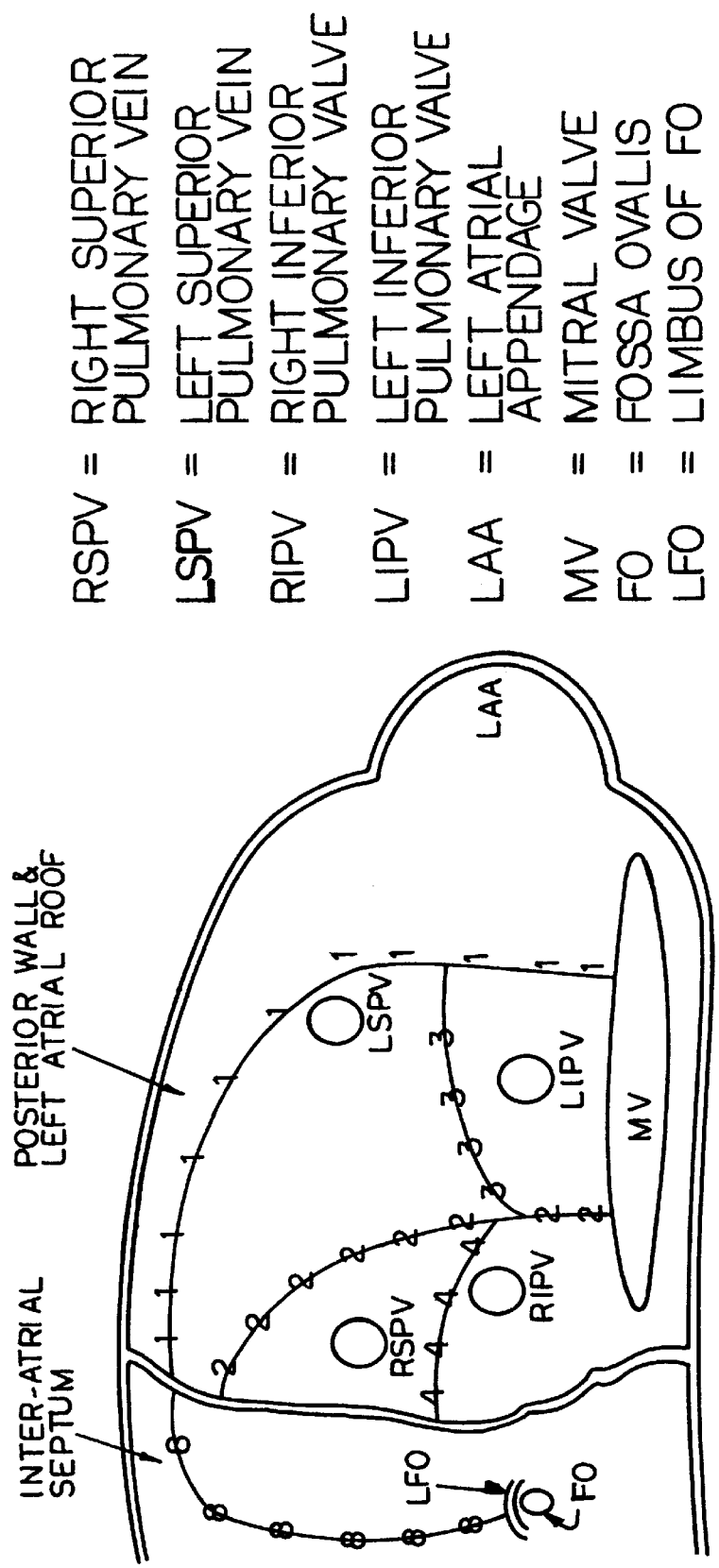

TRACK#1

TRACK#2

TRACK#5-RIGHT ATRIUM

TRACK#6-RIGHT ATRIUM

TRACK#7–RIGHT ATRIUM

TRACK#9–RIGHT ATRIUM

TRACK # 8-INTER CATHETER ABLATION

TRACK#8-RIGHT ATRIUM

TRACK#8-LEFT ATRIUM

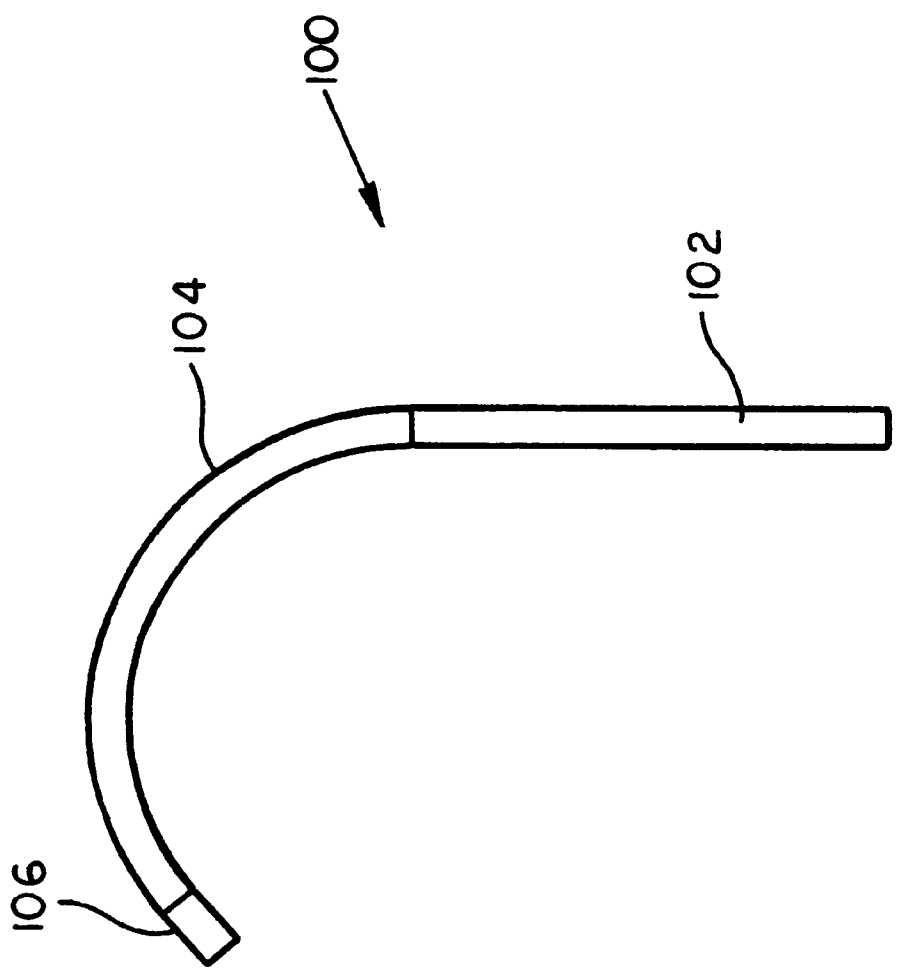
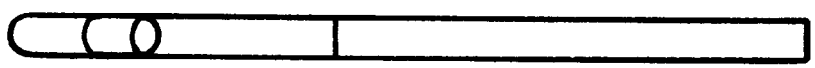
FIG. 16A
FIG. 16B

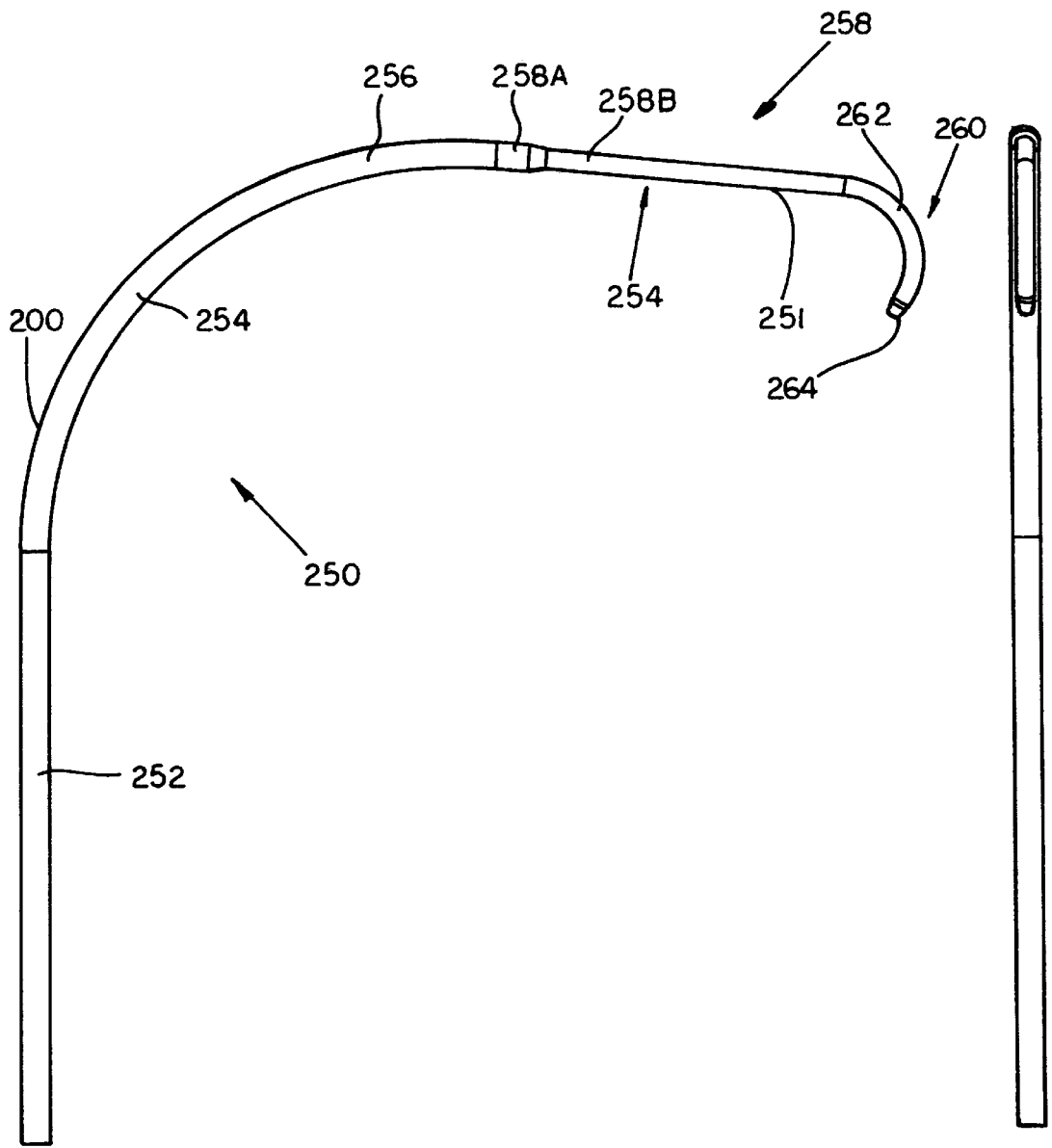

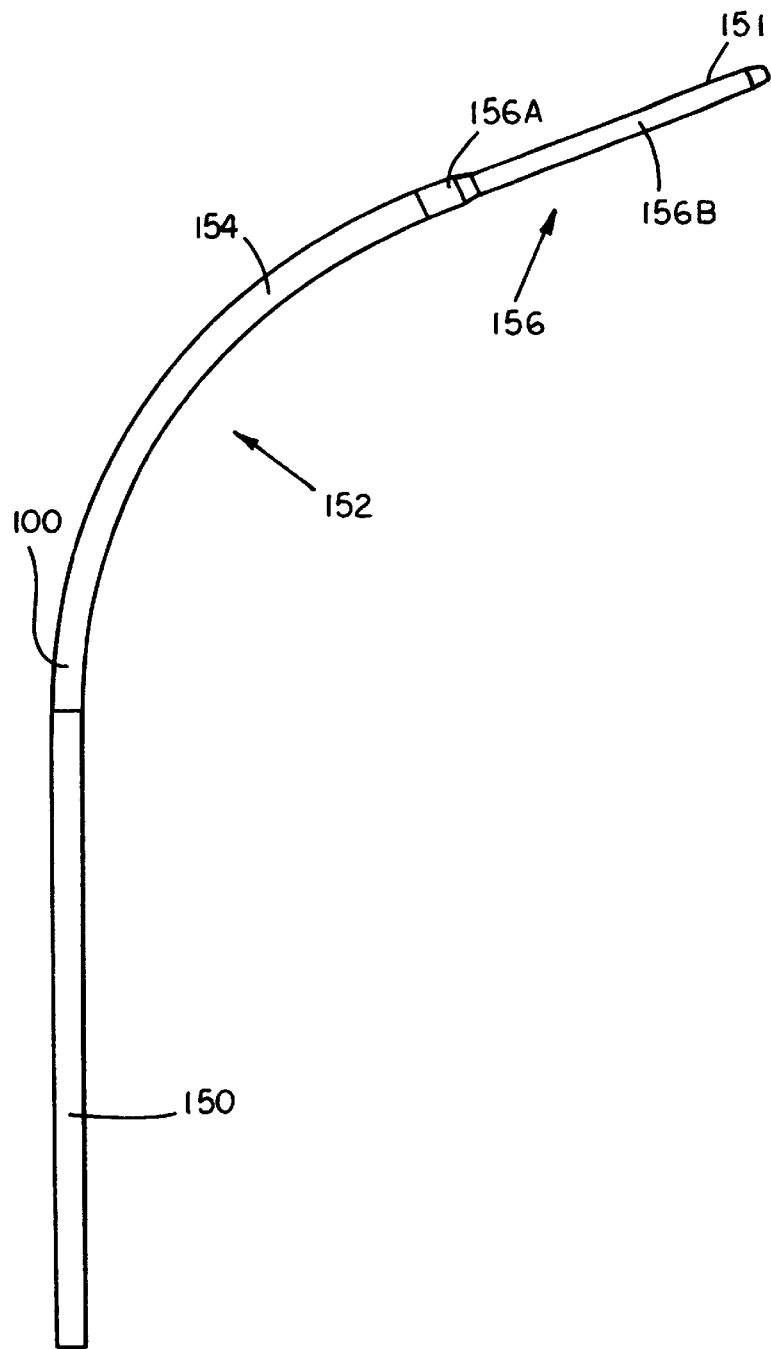
FIG. 20A
FIG. 20B

SHAPED GUIDING INTRODUCERS FOR USE WITH A CATHETER FOR THE TREATMENT OF ATRIAL ARRHYTHMIA

CROSS REFERENCE TO RELATED APPLICATIONS

This application is a continuation-in-part of application Ser. No. 08/949,929, filed Oct. 14, 1997, U.S. Pat. No. 5,902,289, which is a divisional application of Ser. No. 08/337,722, filed Nov. 14, 1994, now U.S. Pat. No. 5,690,611, which is a continuation-in-part of application Ser. No. 08/272,014, filed Jul. 8, 1994, now U.S. Pat. No. 5,575,766.

BACKGROUND OF INVENTION

Introducers and catheters have been in use for medical procedures for many years. For example, one use has been to convey an electrical stimulus to a selected location within the human body. Another use is the monitoring of measurements for diagnostic tests within the human body. Catheters may examine, diagnose and treat while positioned at a specific location within the body which is otherwise inaccessible without more invasive procedures. These catheters are then guided to a specific location for examination, diagnosis or treatment by manipulating the catheter through the artery or vein of the human body.

The utilization of the catheters is frequently limited because of the need for a precise placement of the electrodes of the catheter at the specific location within the body.

Control of the movement of catheters to achieve such precise placement is difficult because of the inherent structure of the catheter. The body of a conventional catheter is long and tubular. To provide sufficient control of the movement of the catheter, it is necessary that its structure be somewhat rigid. However, the catheter must not be so rigid as to prevent the bending or curving necessary for movement through the vein, artery or other body part to arrive at the specified location. Further, the catheter must not be so rigid as to cause damage to the artery or vein while it is being moved within the body.

It is also important that there be sufficient rigidity in the catheter to accommodate torque control, i.e., the ability to transmit a twisting force along the length of the catheter. Sufficient torque control enables controlled maneuverability of the catheter by the application of a twisting force at the proximal end of the catheter that is transmitted along the catheter to its distal end. The need for greater torque control often conflicts with the need for reduced rigidity to prevent injury to the body vessel.

Catheters are used increasingly for medical procedures involving the human heart. In these procedures a catheter is typically advanced to the heart through veins or arteries and then is positioned at a specified location within the heart. Typically, the catheter is inserted in an artery or vein in the leg, neck, upper chest or arm of the patient and threaded, generally with the aid of a guidewire or introducer, through the various arteries or veins until the distal tip of the catheter reaches the desired location in the heart.

The distal end of a catheter used in such a procedure is sometimes preformed into a desired curvature so that by torquing the catheter about its longitudinal axis, the catheter can be guided to the desired location within the heart or in the arteries or veins associated with the heart.

Catheter assemblies have also been designed wherein a catheter having a predetermined curve is received within a sheath that is advanced over the distal end of the catheter. Advancement of the catheter within the sheath modifies the predetermined curve of the distal end of the catheter. See U.S. Pat. Nos. 5,290,229, 5,267,982, 5,304,131 and 4,935,017. By inserting different shaped guide catheters through the outer guide catheter, different shapes for the distal end of the catheter are created. Inner and outer guide catheters are also disclosed, for example, in U.S. Pat. Nos. 5,304,131, 5,279,546, 5,120,323 and 4,810,244 and 5,290,229.

Atrial fibrillation is the most common sustained heart arrhythmia. It is estimated to occur in upwards of 0.4 percent of the adult population and perhaps as many as 10 percent of the population who are 60 years or older. Cox, J. L., et al., *Electrophysiology, Pacing and Arrhythmia*, "Operations for Atrial Fibrillation," Clin. Cardiol. 14, 827–834 (1991). Atrial arrhythmia may be transient or persistent. While most atrial arrhythmia occurs in individuals having other forms of underlying heart disease, some atrial arrhythmias occur independently. While atrial arrhythmias do not directly cause death as frequently as ventricular arrhythmias, they increase the risk factor for a number of other diseases such as strokes, thrombosis, atherosclerosis, systemic and cerebral embolism and cause a number of additional medical problems.

Another treatment for atrial arrhythmia or fibrillation involves the use of an implanted atrial defibrillator or cardioversion. See, for example, U.S. Pat. Nos. 5,282,836, 5,271,392 and 5,209,229. See also Martin, D., et al., *Atrial Fibrillation*, pp. 42–59 (1994).

Certain patients with symptomatic or life threatening atrial arrhythmias, however, cannot be adequately treated by drugs or these medical devices. Other forms of aggressive treatment are mandated, which may include surgery. For example, a surgical procedure for the treatment of atrial arrhythmia known as the "Maze" procedure is disclosed in Cox, J. L. et al., *Electrophysiology, Pacing and Arrhythmia*, "Operations for Atrial Fibrillation," Clin. Cardiol. 14, 827–834 (1991). See also Cox, J. L., et al., "The Surgical Treatment of Atrial Fibrillation," *The Journal of Thoracic and Cardiovascular Surgery*, Vol. 101, No. 4, pp. 584–592, 569–583 (April, 1991), and Cox, J. L., et al., "The Surgical Treatment of Atrial Fibrillation," *The Journal of Thoracic and Cardiovascular Surgery*, Vol. 101, No. 4, pp. 406–426 (March, 1991). Other surgical procedures for atrial arrhythmia are disclosed, for example, in Martin, D., et al., *Atrial Fibrillation*, pps. 54–56 (1994). Another procedure used for certain types of cardiac arrhythmia (but not atrial fibrillation) within the last 10 to 15 years is catheter ablation. This procedure has been used to interrupt or modify existing conduction pathways associated with ventricular arrhythmias within the heart. The particular area for ablation depends on the type of underlying ventricular arrhythmia. One common ablation procedure is for the treatment of atrioventricular (AV) nodal reentrant tachycardia. With this problem ablation of the fast or slow AV nodal pathways has become an accepted treatment. See Singer, I., et al., "Catheter Ablation for Arrhythmias" *Clinical Manual of Electrophysiology*, pp. 421–431 (1993); Falk, R. H., et al., *Atrial Fibrillation Mechanisms in Management*, pp. 359–374 (1992); Horowitz, L. N., *Current Management of Arrhythmias*, pp. 373–378 (1991); and Martin, D., et al., *Atrial Fibrillation*, pp. 42–59 (1994). The use of ablation catheters for ablating locations within the heart has also been disclosed, for example in U.S. Pat. Nos. 4,641,649, 5,263,493, 5,231,995, 5,228,442 and 5,281,217. However, none utilize a guiding introducer to guide the ablation catheter to a particular location within the heart.

Catheter ablation of accessory pathways associated with Wolfe-Parkinson-White syndrome using a long vascular sheath using both a transseptal and retrograde approach is discussed in Saul, J. P., et al. "Catheter Ablation of Accessory Atrioventricular Pathways in Young Patients: Use of long vascular sheaths, the transseptal approach and a retrograde left posterior parallel approach" *Journal of the American College of Cardiology*, Vol. 21, no. 3, pps. 571–583 (Mar. 1, 1993). See also Swartz, J. F. "Radiofrequency Endocardial Catheter Ablation of Accessory Atrioventricular Pathway Atrial Insertion Sites" *Circulation*, Vol. 87, no. 2, pps. 487–499 (February, 1993).

The sources of energy used for catheter ablation vary. Initially, high voltage, direct current (DC) ablation techniques were commonly used. However, because of problems associated with the use of DC current, radio frequency (R.F.) ablation has become a preferred source of energy for some ablation procedures. The use of RF energy for ablation has been disclosed, for example, in U.S. Pat. Nos. 4,945,912, 5,209,229, 5,281,218, 5,242,441, 5,246,438, 5,281,213 and 5,293,868. Other energy sources being considered for ablation of heart tissue include laser, ultrasound, microwave and direct current (low energy and fulgutronization). Also shown have been procedures where the temperature of the surrounding fluid about the catheterization probe is reduced.

In addition, the use of radio frequency ablation energy for the treatment of Wolfe-Parkinson-White syndrome in the left atrium by use of a transseptal sheath is disclosed in Swartz, J. F. et al. "Radiofrequency Endocardial Catheter Ablation of Accessory Atrioventricular Pathway Atrial Insertion Sites" *Circulation* 87:487–499 (1993). See also Tracey, C. N. "Radio Frequency Catheter Ablation of Ectopic Atrial Tachycardia Using Paced Activation Sequence Mapping" J. Am. Coll. Cardiol. 21:910–917 (1993).

Ablation of a precise location within the heart requires the precise placement of the ablation catheter within the heart. Precise positioning of the ablation catheter is especially difficult because of the physiology of the heart, particularly as the ablation procedures generally occur while the heart is beating. Commonly, the placement of the catheter is determined by a combination of electrophysiological guidance and fluoroscopy (placement of the catheter in relation to known features of the heart which are marked by radiopaque diagnostic catheters which are placed in or at known anatomical structures such as the coronary sinus, high right atrium and the right ventricle).

While these techniques have been useful for certain arrhythmias, catheter ablation for treatment of atrial fibrillation within the atria has not been disclosed. At best, procedures for ablation of the AV node or the His-Purkinje bundle have been disclosed, for example in U.S. Pat. No. 4,641,649 and Martin, D., et al., *Atrial Fibrillation*, p. 53 (1994).

SUMMARY OF INVENTION

The instant invention is a process for the treatment and/or mapping of atrial arrhythmia by the use of mapping and/or ablation catheters comprising:

introducing into the atria a mapping or ablation catheter placed within shaped, guiding introducers and mapping or ablating a selected area within the atria.

One preferred embodiment of the invention is a process for the treatment and/or mapping of atrial arrhythmia comprising:

(1) introducing a shaped, guiding introducer into the right atrium of a human heart;

(2) positioning an ablation and/or mapping catheter within the right atrium using the shaped, guiding introducer;

(3) ablating and/or mapping a preselected track within the right atrium by use of the ablation and/or mapping catheter located within the shaped, guiding introducer;

(4) repeating steps (1), (2) and (3) using the same or a different shaped, guiding introducer to ablate and/or map a plurality of preselected tracks within the right atrium, to reduce or eliminate reentry circuits within the right atrium;

(5) introducing a shaped, guiding introducer into the left atrium of a human heart;

(6) positioning an ablation and/or mapping catheter within the left atrium using the shaped, guiding introducer;

(7) ablating and/or mapping a preselected track within the left atrium by use of the ablation catheter located within the shaped, guiding introducer;

(8) repeating steps (5), (6) and (7) using the same or a different shaped, guiding introducer to ablate and/or map a plurality of preselected tracks within the left atrium, to reduce or eliminate reentry circuits within the left atrium; thereby creating a generally uninterrupted pathway or corridor for electrical impulses from the sinoatrial node to the atrioventricular node, while permitting more or less complete atrial contraction and atrioventricular synchrony.

In another preferred embodiment specifically designed shapes for the guiding introducers for use with mapping and/or ablation catheters in the mapping and/or treatment of atrial arrhythmia are disclosed. In particular, five shaped guiding introducers, each with a different shape, are disclosed for procedures within the left atrium and four shaped guiding introducers are disclosed for procedures within the right atrium.

In another preferred embodiment, one or more of the individual guiding introducers previously discussed are replaced by a guiding introducer system comprised of a pair or more of guiding introducers which work in combination to provide more flexibility to the physician in the ablation of selected locations within the Lou atria of the heart. In particular, a guiding introducer system comprised of a pair of guiding introducers is used to assist the ablation and/or mapping catheter within the left atrium of the heart for the ablation and/or mapping of preselected locations within the left atrium.

BRIEF DESCRIPTION OF THE DRAWINGS

FIG. 2 is a detailed drawing of the left atrium showing the preferred ablation tracks.

FIG. 3I is a schematic drawing of the interatrial septum showing the use of guiding introducers for simultaneous ablation in the left and right atrium as shown in FIGS. 4A and B for the right atrium and FIGS. 7A, B and C or, alternatively, FIGS. 8A and B, for the left atrium to produce the two parallel tracks designated as track 8.

FIG. 16A is a side view of an outer guiding introducer for use in the left atrium as part of an alternative guiding introducer system.

FIG. 16B is a front view of the outer guiding introducer for use in the left atrium as shown in FIG. 16A rotated 90° clockwise from the position of FIG. 16A.

FIG. 19A is a side view of the outer guiding introducer disclosed in FIGS. 17A and 17B utilized in combination with the inner guiding introducer as shown in FIGS. 14A and 14B, wherein the curved portion of the inner guiding introducer is extended from a distal end of the outer guiding introducer.

FIG. 19B is a front view of the combination of outer guiding introducer and inner guiding introducer as shown in FIG. 19A rotated 90° clockwise from its position in FIG. 19A.

FIG. 20A is a side view of the outer guiding introducer disclosed in FIGS. 16A and 16B utilized in combination with a straight, uncurved guiding introducer, wherein a portion of the inner guiding introducer is extended from a distal end of the outer guiding introducer.

FIG. 20B is a front view of the combination of the outer guiding introducer and inner guiding introducer as shown in FIG. 20A rotated 90° clockwise from its position in FIG. 20A.

DETAILED DESCRIPTION OF THE PREFERRED EMBODIMENT

This invention relates to a process for the mapping and treatment of atrial arrhythmia using a catheter guided by shaped guiding introducers. In addition, it relates to the preferred shape of the guiding introducers which are used with a catheter for the mapping or treatment of atrial arrhythmias. In addition, it relates to a guiding introducer system preferably comprised of an inner and an outer guiding introducer used in combination with a mapping and/or ablation catheter for the treatment of atrial arrhythmia and the overall shape of the combination of inner and outer guiding introducers.

Figure 1:
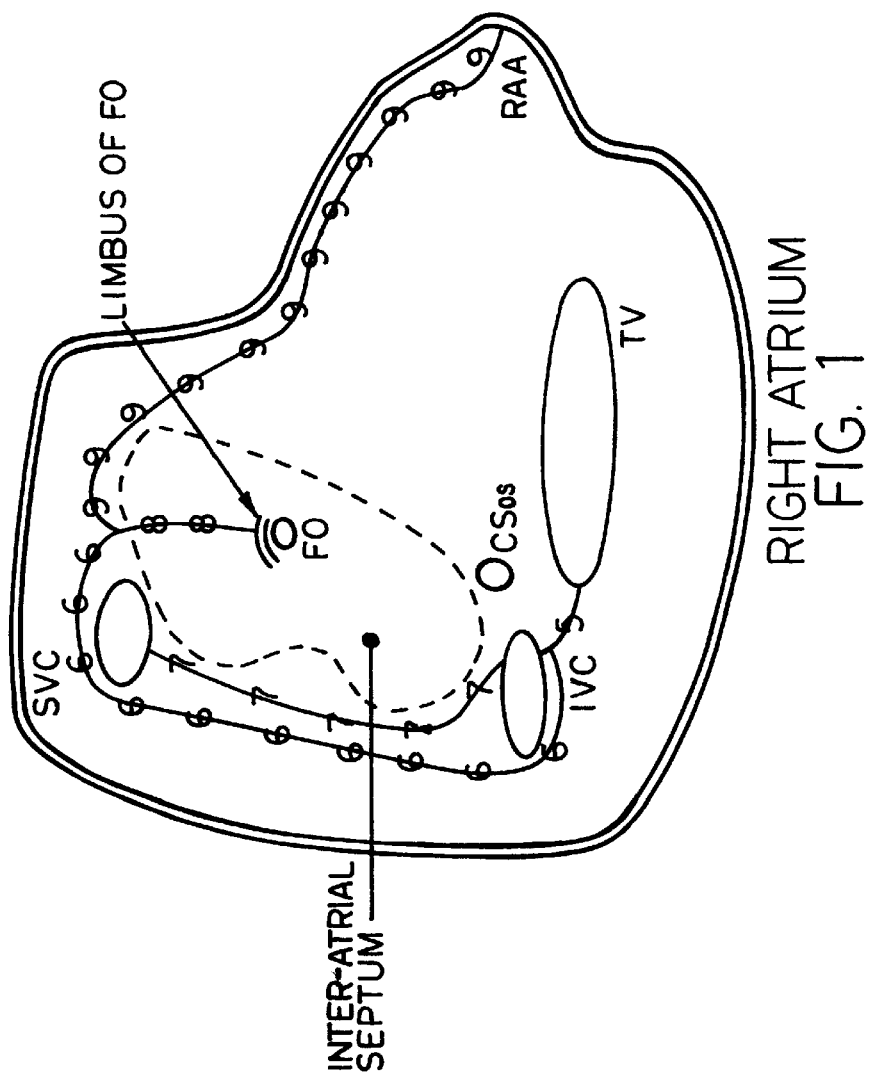
FIG. 1 is a detailed drawing of the right atrium showing the preferred ablation tracks.

A typical human heart includes a right ventricle, a right atrium, left ventricle and left atrium. The right atrium is in fluid communication with the superior vena cava and the inferior vena cava. The atrioventricular septum separates the right atrium from the right ventricle. The tricuspid valve contained within the atrioventricular septum communicates the right atrium with the right ventricle. On the inner wall of the right atrium where it is connected with the left atrium is a thin walled, recessed portion, the fossa ovalis. A detailed schematic drawing of the right atrium is shown in FIG. 1 and a detailed schematic drawing of the left atrium is shown in FIG. 2. In the heart of a fetus, the fossa ovalis is open (patent foramen), permitting fetal blood to flow between the right and left atria. In most individuals, this opening closes after birth, but in as many as 25 percent of individuals an opening (the patent foramen) still remains in place of the fossa ovalis between the right and left atria. Between the fossa ovalis and the tricuspid valve is the opening or ostium for the coronary sinus. The coronary sinus is the large epicardial vein which accommodates most of the venous blood which drains from the myocardium into the right atrium.

In the normal heart, contraction and relaxation of the heart muscle (myocardium) takes place in an organized fashion as electrochemical signals pass sequentially through the myocardium from the sinoatrial (SA) node to the atrialventricular (AV) node and then along a well defined route which includes the His-Purkinje system into the left and right ventricles. Initial electric impulses are generated at the SA node and conducted to the AV node. The AV node lies near the ostium of the coronary sinus in the interatrial septum in the right atrium. The His-Purkinje system begins at the AV node and follows along the membranous interatrial septum toward the tricuspid valve through the atrioventricular septum and into the membranous interventricular septum. At about the middle of the interventricular septum, the His-Purkinje system splits into right and left branches which straddle the summit of the muscular part of the interventricular septum.

Sometimes abnormal rhythms occur in the atrium which are referred to as atrial arrhythmia. Three of the most common arrhythmia are ectopic atrial tachycardia, atrial fibrillation and atrial flutter. Atrial fibrillation can result in significant patient discomfort and even death because of a number of associated problems, including: (1) an irregular heart rate which causes the patient discomfort and anxiety, (2) loss of synchronous atrioventricular contractions which compromises cardiac hemodynamics resulting in varying levels of congestive heart failure, and (3) stasis of blood flow, which increases the likelihood of thromboembolism. It is sometimes difficult to isolate a specific pathological cause for atrial fibrillation although it is believed that the principle mechanism is one or a multitude of reentry circuits within the left and/or right atrium.

Efforts to alleviate these problems in the past have included significant usage of pharmacological treatments. While pharmacological treatments are sometimes effective, in some circumstances drug therapy is ineffective and frequently is plagued with side effects such as dizziness, nausea, vision problems and other difficulties.

In the last few years surgical procedures have also been utilized in the treatment of atrial arrhythmia. The goal of these surgical procedures parallel that of the pharmacological treatments, to relieve both the subjective symptoms of atrial arrhythmia as well as to normalize hemodynamics by restoring regular atrial contributions to the cardiac output. One method suggested requires isolation of the left atrium from the remainder of the heart by a surgical procedure. See Cox, J. L., et al., "The Surgical Treatment of Atrial Fibrillation," *J. Thoracic and Cardiovascular Surgery*, Vol. 101, No. 4, p. 570 (1991). The initial incisions followed by the scar tissue left by such surgery effectively isolates the left atrium and, in some cases, provides some relief for the patient. Such relief can occur as long as the right atrium maintains adequate sinus rhythm. Various problems associated with this procedure, other than the maintenance of appropriate sinus rhythm, include thromboembolic risks.

Another procedure for treatment of atrial arrhythmia involves the ablating of the His bundle. A permanent pacemaker is then installed, resulting in a regular ventricular beat. See Cox, J. L., et al., "The Surgical Treatment of Atrial Fibrillation," *Journal of Thoracic and Cardiovascular Surgery*, Vol. 101, No. 4, pp. 570–572 (1991). However, because the atria may continue to fibrillate, normal cardiac hemodynamics are not restored and there is still vulnerability to thromboembolism.

A newer surgical procedure designed by Guiraudon in 1985 results in the creation of a narrow corridor between the SA node and the AV node. See Guiraudon, G. M., et al, *Combined Sinoatrial Node/Atrial Ventricular Node Isolation: a Surgical Alternative to His Bundle Ablation in Patients with Atrial Fibrillation*; Circulation 72:(pt-2) III-220 (1985). This procedure isolates a narrow corridor from the remainder of the atrial muscle tissue and can, in some circumstances, alleviate some of the problems associated with the atrial arrhythmia.

A more recent, more complex surgical procedure, the "Maze" procedure, has also been designed to treat atrial arrhythmia. See Cox, J. L., et al., "The Surgical Treatment of Atrial Fibrillation," *Journal of Thoracic and Cardiovascular Surgery*, Vol 101 pp. 569–83 (1989). Appropriately placed atrial incisions are designed to interrupt the conduction routes of those areas in the atria that produce the most common reentrant circuits. The procedure is also designed to direct the sinus impulse from the sinus node to the AV node along a specified route. After the procedure, the entire atrial myocardium (except for the atrial appendages and pulmonary veins) is designed to be electrically active by providing for multiple blind alleys off the main conduction route between the SA node and the AV node, thereby preserving atrial transport function postoperatively. While this procedure has resulted in successful treatments for certain patients, there are significant potential risks due to the extensive nature of the surgery.

The effectiveness of the "Maze" procedure is dependent upon the destruction of tissue within the atrium along lines or tracks to prevent the formation of reentry circuits while still allowing the atria to contract and permitting the return of normal atrioventricular conductivity. It has been discovered that similar success can be achieved without invasive surgery by the use of ablation procedures performed within the atria. However, to accomplish this procedure the ablation catheter must be positioned at pre-determined locations within the right and left atrium to ablate predetermined tracks within the left and right atria, thus forming a natural barrier to the formation of the reentry circuits. In addition to the necessity of producing ablation tracks in well defined areas of the left and right atria, it is also critical for proper transmural lesion formation that adequate contact pressure be maintained between the ablation catheter electrode and the heart tissue to be ablated.

HOOF The ablation catheters used to perform the ablation procedures produce scar tissue at the selected site within the atria. The energy necessary to scar or ablate the tissue can be provided by a number of different sources. Originally direct current was utilized to provide the energy for ablation procedures. Laser, microwave, ultrasound and other forms of direct current (high energy, low energy and fulgutronization procedures) have also been utilized to perform ablation procedures. The preferred source of energy for the ablation procedures of the instant invention is RF energy.

One of the significant difficulties in performing any cardiac procedure in the atria is caused by the physiology of the atria when beating, especially if that beating is abnormal. The preferred procedure for the creation of ablation tracks within the left and right atria thus requires the precise positioning and contact pressure of the electrodes of the ablation catheter within the atria to ablate a predetermined track in the tissue of the atria. These lesions or tracks may be in the same locations as the incisions in the "Maze" procedure, but may also be positioned at different locations within the atria to produce similar results.

Mere introduction of an ablation catheter into either the left or right atrium without precise placement and precise contact pressure will not be sufficient to allow the creation of the desired ablation tracks. This precise placement and contact pressure cannot be produced without the use of specialized precurved guiding introducers to guide the ablation catheter to the correct location and to permit adequate pressure to be placed on the ablation catheter to produce an adequately ablated track.

An element of treatment of atrial arrhythmia also includes sensing of locations in the atria to efficiently and accurately map the atria. The physiology of the heart and its beating also interferes with the effectiveness of mapping catheters. The guiding introducers of the instant invention can also assist in the precise placement of these mapping catheters.

Medical practitioners often monitor the introduction of cardiac catheters and their progress through the vascular system by use of fluoroscopes. Unfortunately, fluoroscopes can not easily identify specific features in the heart, in general, and the critically important structures of the right and left atrium in specific, thus making placement and utilization of an ablation catheter extremely difficult without the use of guiding introducers. This placement is especially difficult as the beating heart is in motion, resulting in the catheter moving within the atria as blood is being pumped through the heart. The structure and shape of the guiding introducers of the instant invention addresses and solves these problems and permits the precise placement necessary for accurate ablation procedures.

The shaped guiding introducers position the mapping and/or ablation catheter at the precise location necessary for the procedure automatically as a result of their shapes. The specially designed guiding introducers are produced from conventional elongated introducers. Although these guiding introducers are described as having multiple sections, preferably, each of them is produced by a conventional introducer production procedure and formed into a single unitary structure. Additional features of these guiding introducers other than their unique shape include radiopaque tip markers and vents which will be discussed in more detail later.

Although in one preferred embodiment a single guiding introducer is used to assist the catheter in mapping and/or ablating a particular track within either the left or the right atrium, alternatively a guiding introducer system comprised of a pair or three or more guiding introducers may be used in combination. In one preferred embodiment, an inner guiding introducer is placed within the lumen of an outer guiding introducer to form the guiding introducer system wherein the combination of the inner and outer guiding introducers creates a variety of different shapes which provide great flexibility in the system to map and/or ablate large areas of the atria based on the rotation of the inner guiding introducer within the outer guiding introducer along with the extension of the inner guiding introducer within the lumen of the outer guiding introducer. Further, the use of a guiding introducer system permits the medical practitioner to map and/or ablate locations within the atria which have shifted as a result of the enlargement of the heart caused by cardiac illness.

The overall shape of the inner guiding introducer and the outer guiding introducer when used in combination may vary, especially when present inside of the human body. These changes are caused by the thermal properties of the materials and the internal stress that is placed on those introducers. As a result of these factors, the introducers will relax after insertion in the body. However, their overall shape is as discussed within the present application.

Where a single guiding introducer is used for a procedure, each of the guiding introducers are used independently to guide the catheter along a separate track or tracks within the atria. When a pair of guiding introducers, comprised preferably of an inner and outer guiding introducer, is used the catheter which is guided through the lumen of the inner guiding introducer, which itself is located within the lumen of the outer guiding introducer, is directed along a particular track or tracks within the atrium. With the precurved, guiding introducer or guiding introducer system holding the ablation catheter in a predetermined location, the ablation catheter then ablates the predetermined ablation track or a specific site in one or a series of ablation procedures. The ablation procedures can result from the use of one or more electrodes located on the ablation catheter. More than one passage over a track or site may be necessary to fully ablate the track. Sensing elements within the catheter also can be used to sense activity along the track or site. After the ablation procedure is complete, this first shaped guiding introducer or guiding introducer system, if necessary, is removed and a second shaped guiding introducer or guiding introducer system, if necessary, is inserted in place thereof and the procedure is repeated with the ablation catheter to create the next ablation track or site. In some situations the guiding introducer system permits the ablation of more than one ablation track or site without removal of the guiding introducer system. The ablation procedures are then continued until there has been a full and complete ablation of all preselected tracks in the atrium of the heart. The choice of which guiding introducer or introducers to use first and in what order is, of course, determined by the individual medical practitioner.

The choice of the selected tracks or sites within the left and right atrium is determined generally from previous experimental and clinical data which has been gathered on the subject. See, for example, Cox, J. L., et al., "The Surgical Treatment of Atrial Fibrillation" *J. Thoracic Cardiovasc. Surg.*, 101:406–426 (1991). However, adjustment in the location of the ablation tracks or sites and the number of tracks or sites is clearly within the discretion of the medical practitioner. For example, the medical practitioner may choose to isolate completely the left atrium as suggested by Scheinman in *Catheter-Induced Ablation of the Atrioventricular Junction to Control Refractory Supraventricular Arrhythmias*, JAMA 248: 851–5 (1982). Alternatively, the medical practitioner may choose to form a "corridor" between the sino-atrial node and the AV node as suggested by Guiraudon in Guiraudon, G. M., et al., *Combined Sino-Atrial Node Atria-ventricular node isolation: A Surgical Alternative to His Bundle Ablation in Patients with Atrial Fibrillation*, 72 (Pt 2); III 220 (1985). Fewer or more ablation procedures can be performed as determined by the medical practitioner.

While the ablation and mapping procedures may commence either in the left or right atrium first, preferably, the procedures begin in the right atrium, prior to breach of the interatrial septum.

The ablation procedures in the right atrium are designed specifically to prevent the development of or to retard existing atrial flutter. They may also assist in the treatment of other atrial arrhthymia. The ablation tracks for the right atrium are designed to eliminate reentry circuits from forming, particularly around the superior vena cava, the inferior vena cave and the right atrial appendage. FIG. 1 shows a schematic drawing of the preferred ablation tracks within the right atrium listed as tracks 5, 6, 7, 8 and 9. Fewer or more ablation tracks may be created depending on the choice of the medical practitioner. The choice as to which tracks are ablated first is also left to the discretion of the medical practitioner.

The ablation track in the interatrial septum in the right atrium designated as track 8 is preferably produced at the same time that a corresponding ablation track in the interatrial septum in the left atrium is produced. See FIG. 1, track 8, FIG. 2, track 8 and FIGS. 3I, 3J and 3K. The preferred procedure for producing these particular ablation tracks uses intercatheter ablation techniques, one catheter using a particularly preferred guiding catheter or a pair of guiding introducers in combination for use in the left atrium and a second catheter using a particularly preferred guiding introducer or pair of guiding introducers to perform the ablation procedure along the interatrial septum in the right atrium. The track runs from the limbus of the fossa ovalis, superior to the septal roof to join the track produced by the first guiding introducer or pair of guiding introducers for the left atrium (FIG. 2, track 1) and FIG. 1, track 6 in the right atrium. This is possible because the track in the left atrium and that in the right atrium are on opposite sides of the interatrial septum. Preferably these tracks are produced after the remaining right side tracks are produced.

While no specifically shaped guiding introducer or introducers is necessary for this procedure in the right atrium, as it can be done using conventional fluoroscope techniques, a guiding introducer with the minimal curve is preferably used to guide the catheter along track 8 in the right atrium. See FIG. 1. The guiding introducer to produce this track within the right atrium is preferably divided into two sections. Each section is preferably merged with the remaining section to form a continuous guiding introducer, preferably formed in a single production process. See FIGS. 4A and 4B and FIGS. 3I and 3J. This guiding introducer is the same guiding introducer disclosed in FIG. 2 of U.S. Pat. No. 5,427,119, which patent is incorporated herein by reference. The first section of this guiding introducer is a conventional, generally elongated hollow straight introducer section of sufficient length for introduction into the patient and for manipulation from the point of insertion to the specific desired location within the right atrium of the heart. Merged with the distal end of the first section of this guiding introducer is a second section which is comprised of a curved section curving to the left as shown in FIG. 4A. The angle of this curve is from M about 45° to about 55° and preferably about 60°. The radius of the curve is from about 0.50 in. (1.2 cm.) to about 2.00 in. (5.1 cm.) and preferably from 1.00 in. (2.5 cm.) to about 2.00 in. (5.1 cm.) The overall length of this curved section is from about 0.20 in. (0.5 cm.) to about 2.00 in. (5.1 cm.) and preferably from about 0.50 in. (1.2 cm.) to about 1.00 in. (2.5 cm.). The third section of the guiding introducer is merged with the distal end of the second section. The third section is comprised of a generally straight section directed at an angle of about 40° to about 60° from the direction of the first section as shown in FIG. 4A and has an overall length of about 0.50 in. (1.2 cm.) to about 3.00 in. (7.7 cm.).

Figure 7C:
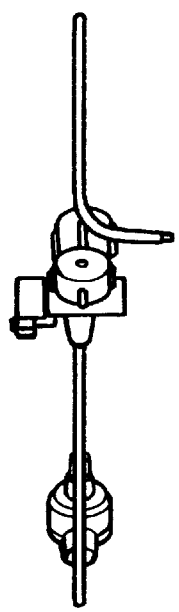
FIG. 7C is a third perspective view of the first guiding introducer for the left atrium rotated 180° from the position of FIG. 7B such that the side port tubing covers a portion of the first guiding introducer.
Figure 7A:
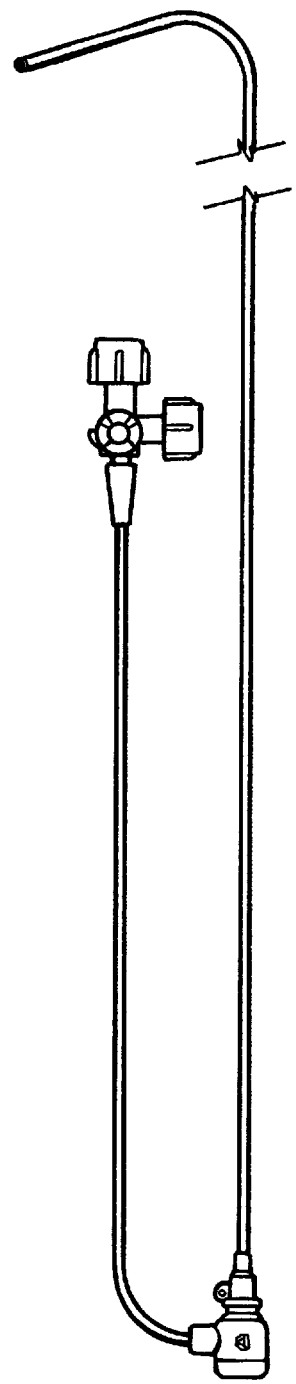
FIG. 7A is a first view of the first guiding introducer for the left atrium for use as shown in FIGS. 3A, 3I and 3K to produce track 1 and track 8 in the left atrium with the side port tubing, which is attached to the proximal end of the guiding introducer, directly to the left of the guiding introducer but generally in the same plane thereof.
Figure 7B:
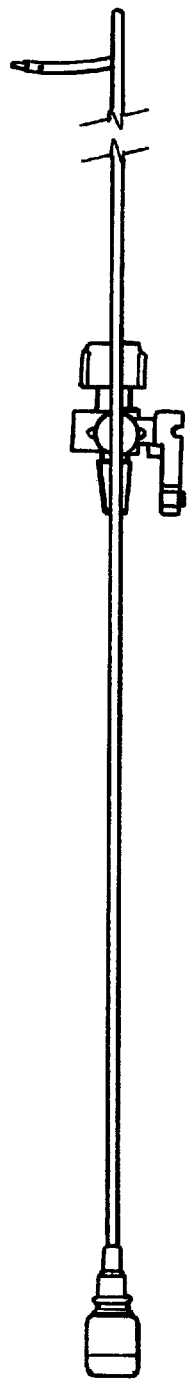
FIG. 7B is a second view of the first guiding introducer for the left atrium as shown in FIG. 7A rotated 90° counterclockwise such that the guiding introducer is positioned over the side port tubing.

The ablation track of the left atrium which is produced at the same time as the ablation track for the right atrium, shown as track 8 on FIG. 2, is made beginning at the limbus of the fossa ovalis superior to the septal roof to join track number 1 shown on FIG. 2. This track is also designated as track 8 on FIG. 3K. The guiding introducer used to produce this track within the left atrium is shown in FIGS. 7A, 7B and 7C. The first section of this guiding introducer is a conventional, generally elongated hollow, straight section of sufficient length for introduction into the patient and for manipulation from the point of insertion to the i specific desired location within the left atrium of the heart. X Merged with the distal end of the first section of this guiding In introducer is the second section which is comprised of a curved section followed by a straight section. The curved section is curved to the left when placed in the position shown in FIG. 7A. The inner angle of this curve is from about 60° to about 80° and more preferably from about 65° to about 75°. The radius of this curve is from about 0.30 in. (0.7 cm.) to about 0.70 in. (1.8 cm.) and preferably from about 0.40 in. (1.0 cm.) to about 0.60 in. (1.5 cm.) At the end of this curve is the straight section which is from about 0.40 in. (1.0 cm.) to about 1.00 in. (2.5 cm.) in length and preferably from about 0.40 in. (1.0 cm.) to about 0.85 in. (2.2 cm.). The third section of this guiding introducer is merged with the distal end of the straight section of the second section. The third section is comprised of a curved section followed by a straight section. The curved section curves backward in relation to the first section as shown in FIG. 7A at an angle of about 80° to about 100° as shown in FIGS. 7B and 7C and preferably from about 85° to about 95° with a radius of about 0.20 in. (0.5 cm.) to about 0.40 in. (1.0 cm.) and preferably from about 0.25 in. (0.6 cm.) to about 0.35 in. (0.9 cm.). At the end of this curve is the final straight section whose length is from about 0.25 in. (0.6 cm.) to about 0.65 in. (1.7 cm.) and preferably from about 0.40 in. (1.0 cm.) to about 0.50 in. (1.3 cm.), ending in the distal tip of the guiding introducer.

Alternatively, to produce track 8 in the left atrium, the guiding introducer as disclosed in U.S. Pat. No. 5,497,774, FIG. 3, which patent is incorporated by reference, may be used.

Figure 8A:
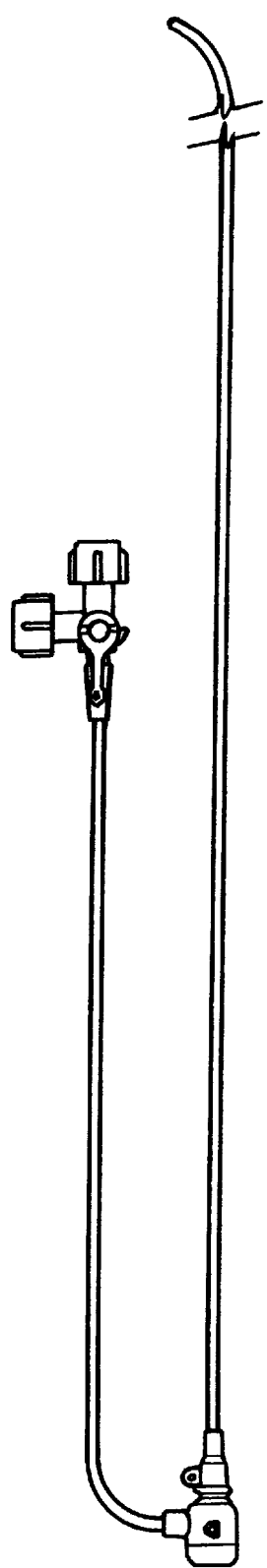
FIG. 8A is the first view of an alternative guiding introducer for the left atrium to that shown in FIGS. 7A, 7B and 7C for use as shown in FIGS. 3I and 3K to produce track 8 in the left atrium with the side port tubing, which is attached to the proximal end of the guiding introducer, directly to the left of the guiding introducer and generally in the same plane thereof.
Figure 8B:
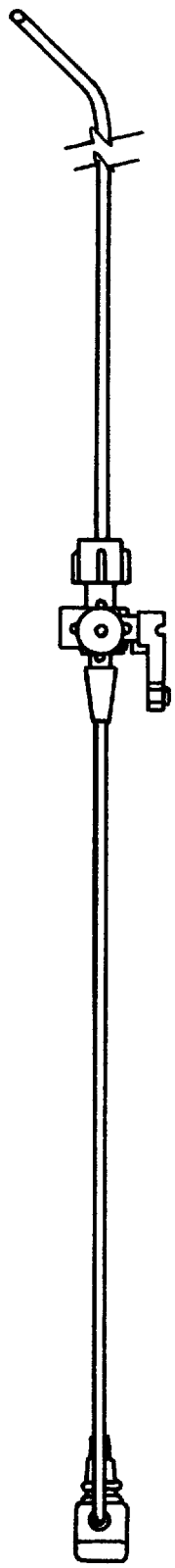
FIG. 8B is the second view of the guiding introducer for the left atrium as shown in FIG. 8A rotated 90° clockwise such that the side port tubing covers a portion of the first portion of the guiding introducer.

This guiding introducer is comprised of a first, second and third section. See FIGS. 8A and 8B. The first section is a conventional, generally elongated hollow, straight introducer section of sufficient length for introduction into the patient and for manipulation from the point of insertion to the specific desired location within the heart. Merged with the distal end of the first section of the guiding introducer is the second section which is curved in a compound curve curving first upward in a first longitudinal curve and simultaneously curving to the left in a second longitudinal curve. The first longitudinal curve has a radius of from about 0.50 in. (1.2 cm.) to about 2.00 in. (5.1 cm.) and preferably from about 0.50 in. (1.2 cm.) to about 1.50 in. (3.8 cm.). The arc of the first longitudinal curve is preferably from about 40° to about 60° and more preferably from about 45° to about 55°. The second longitudinal curve of the second section contains a radius from about 0.50 in. (1.2 cm.) to about 4.00 in. (10.2 cm.) and preferably from about 0.50 in. (1.2 cm.) to about 2.00 in. (5.1 cm.). The third section of the guiding introducer is a third longitudinal curve wherein the plane of the third section is angled upward at an angle of approximately 40° to about 60° and preferably about 45° to about 55°, wherein substantially all of said third section co-planar (at least within 15° coplanar). The arc of this longitudinally curved portion of the third section has an arc of about 35° to about 55°, preferably from 40° to about 50°.

Alternatively, to produce track 8 in the left atrium, a guiding introducer system may be used comprised of an inner and an outer guiding introducer. See FIGS. 12A, 12B, 13A and 13B. A conventional dilator is used with this guiding introducer system for this cardiac procedure. The standard length of this dilator is from about 70 cm. to 90 cm.

Figure 22:
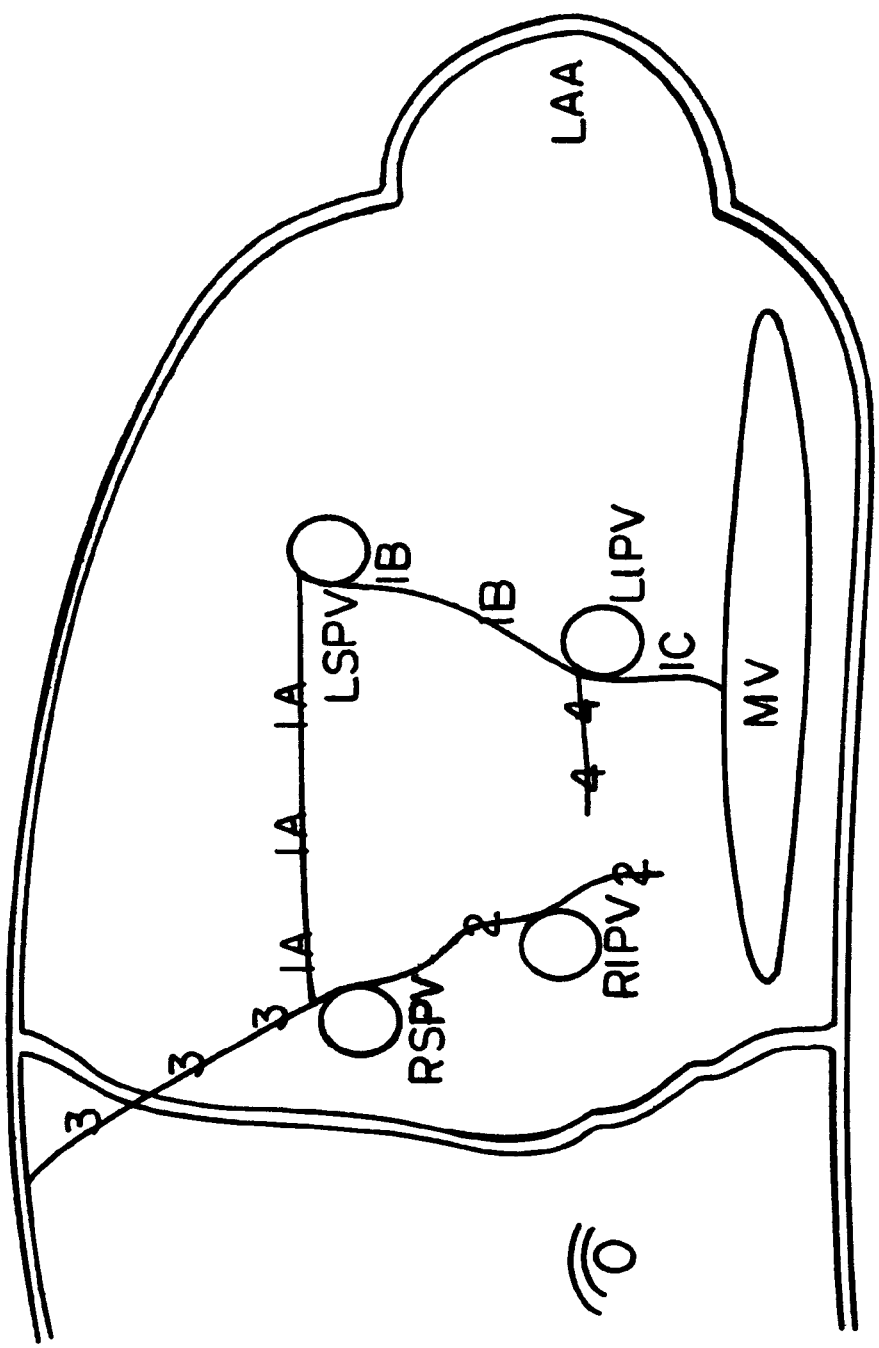
FIG. 22 is a schematic drawing of the left atrium showing a series of alternative preferred ablation tracks.

Alternatively, referring to FIG. 22, ablation tracks numbers 1, 2, 3 and 4 are shown in the left atrium. Track 1 is comprised of three (3) sub tracks, 1a, 1b, and 1c. Track 1a connects points on the superior aspects of the left and right superior pulmonary veins (LSPV, RSPV). Track 1b connects track 1a at the left superior pulmonary vein (LSPV) to the ostium of the left inferior pulmonary vein (LIPV). Track 1c connects the point at the ostium of the left inferior pulmonary vein (LIPV) to the mitral valve (MV) annulus just inferior to the left inferior pulmonary vein (LIPV). Track 2 connects from the point at the right superior pulmonary vein (RSPV) where track 1 began to the ostium of the right inferior pulmonary vein (RIPV) and inferior but stops short of the mitral valve (MV) annulus. Track 3 extends from the point of the right superior pulmonary vein (RSPV) which is the intersection of track 1a and track 2 to the left fibrous trigone. Track 4 extends from the point on the ostium of the left inferior pulmonary vein (LIPV) (intersection of tracks 1b and 1c) towards the right inferior pulmonary vein (RIPV) but stopping short of track 2. Additional track schemes may be discovered which will also be within the contemplation of the invention.

Figures 12A, 12B:
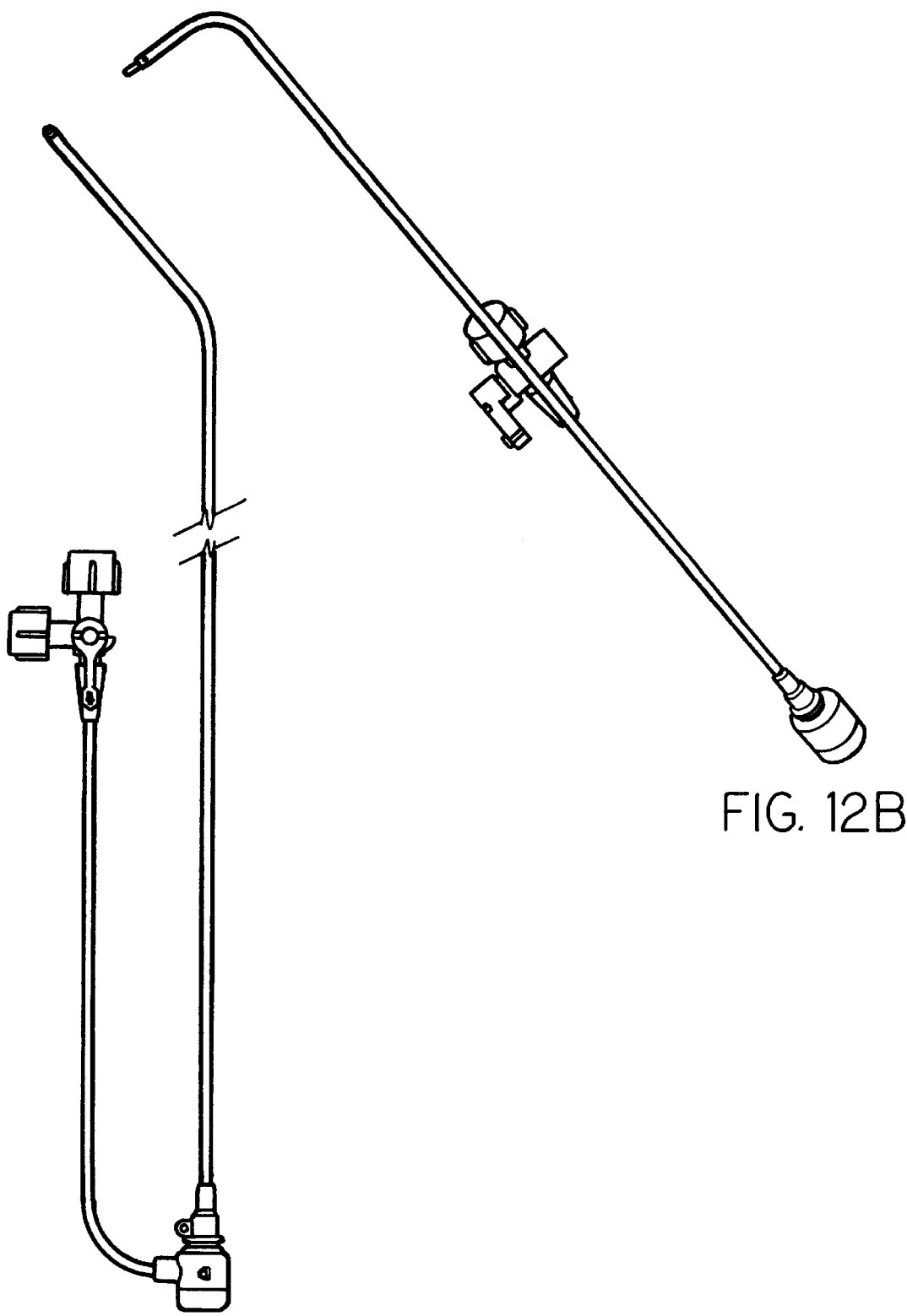
FIG. 12A is a first view of the inner guiding introducer for use in the left atrium as part of an alternative guiding introducer system to produce the tracks shown in FIGS. 3A, 3B, 3I and 3K defined as tracks 1, 2 and/or 8, wherein the side port of the inner guiding introducer which is attached to the proximal end of the inner guiding introducer, is directed to the left of the inner guiding introducer, but generally in the same plane thereof.
FIG. 12B is a second view of the inner guiding introducer for use in the left atrium as shown in FIG. 12A rotated 90° clockwise from the position of FIG. 12A such that the side port is directed behind the first section of the inner guiding introducer and also rotated approximately 40° upward and to the right about the distal tip of the guiding introducer.
Figures 13A, 13B:
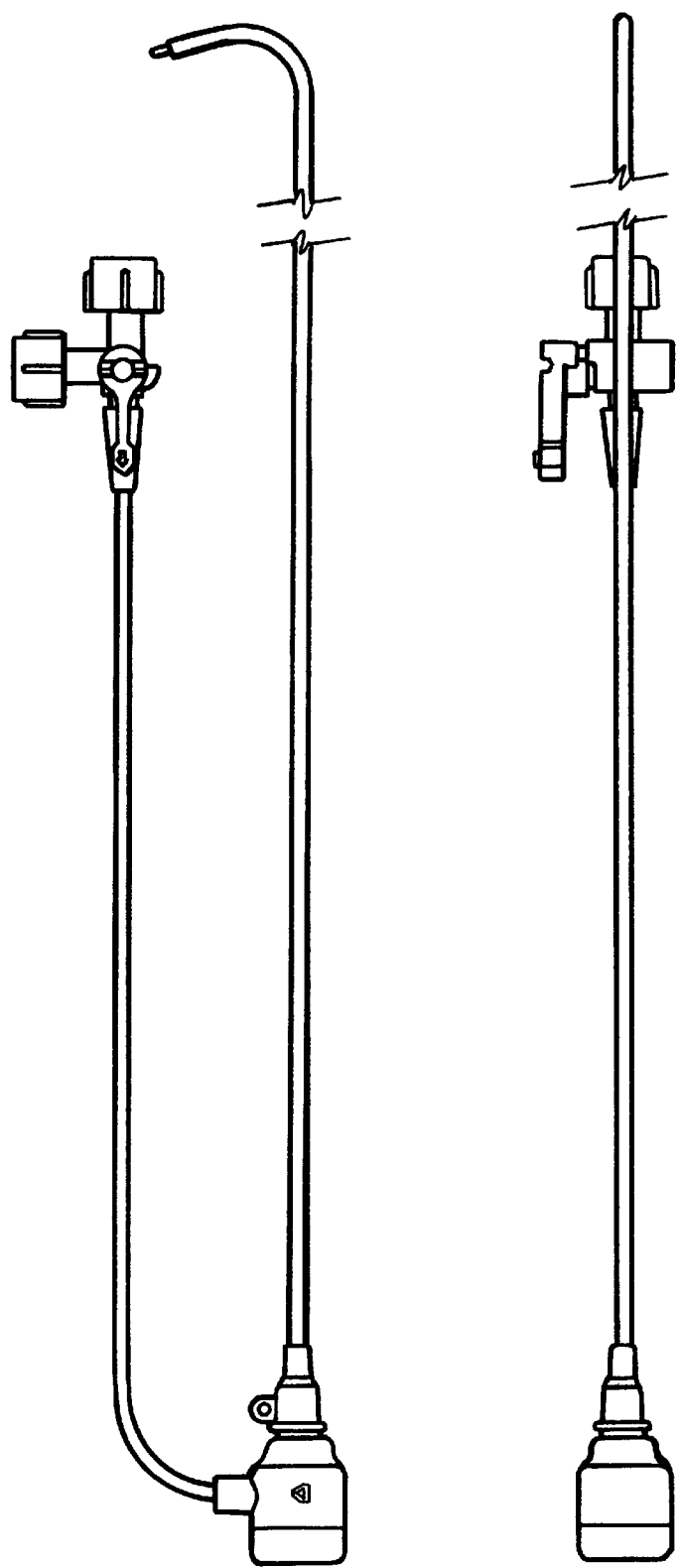
FIG. 13A is a first view of the outer guiding introducer for use in the left atrium as part of an alternative guiding introducer system to be used in combination with the inner guiding introducer of FIGS. 12A and 12B to produce the tracks shown in FIGS. 3A, 3B, 3I and 3K defined as tracks 1, 2 and/or 8, wherein the side port of the outer guiding introducer, which is attached to the proximal end of the guiding introducer, is directed to the left of the outer guiding introducer, but generally in the same plane thereof.
FIG. 13B is a second view of the outer guiding introducer for use in the left atrium as shown in FIG. 13A rotated 90° clockwise from the position of FIG. 13A such that the side port is directed behind the first section of the outer guiding introducer.

The inner guiding introducer is generally comprised of three sections. See FIGS. 12A and 12B. (The position of the inner guiding introducer as shown in FIG. 12A is first rotated about its axis 90° such that the side port tubing is directed behind the inner guiding introducer and then rotated approximately 40° upward and to the right about the distal end to produce FIG. 12B. These positions best disclose the shape of the inner guiding introducer.) The first section is a conventional, generally elongated hollow straight introducer section of sufficient length for introduction into the patient and for manipulation from the point of insertion to the specific desired location within the heart. Merged with the distal end of the first section of the guiding introducer, but an integral part of the entire guiding introducer, is the second section which is comprised of two portions, a curved portion followed by a straight portion. The curved portion is curved in a simple curve to the left as shown in FIG. 12A with a radius of Emi about 0.4 in. (1.0 cm.) to about 0.8 in. (2.0 cm.), preferably 0.6 in. (1.5 cm.) to 0.7 in. (1.8 cm.) to form an arc of about 110° to 170°, preferably from about 130° to about 150°. The straight portion of the second section is about 1.0 in. (2.5 cm.) to about 2.0 in. (5.1 cm.) in length and preferably about 1.4 in. (3.5 cm.) to about 1.7 in. (4.3 cm.) in length. The first and second sections are substantially coplanar as shown in FIG. 12B. Merged with the distal end of the second section is the third section of the inner guiding introducer, which is comprised of a curved portion followed by a straight portion, wherein the curved portion is curved to the left as shown in FIG. 12B with a radius of about 0.1 in. (0.2 cm.) to about 0.5 in. (1.3 cm.) and preferably from about 0.25 in. (0.6 cm.) to about 0.35 in. (0.9 cm.) with an arc of about 70° to about 110°, preferably about 80° to about 100°. The straight portion of the third section follows the curved portion and is from about 0.5 in. (1.2 cm.) to about 1.0 in. (2.5 cm.) and preferably from about 0.7 in. (1.8 cm.) to about 0.8 in. (2.0 cm.) ending in the distal tip of the inner guiding introducer.

The outer guiding introducer for use with the inner guiding introducer in the left atrium as shown in FIGS. 12A and 12B is comprised of first and second sections. See FIGS. 13A and 13B. As with the inner guiding introducer, this outer guiding introducer is divided into separate sections for ease of illustration. The guiding introducer is preferably formed in a single procedure with each section an integral part of the overall outer guiding introducer. The first section of the outer guiding introducer is a conventional generally elongated straight introducer section of sufficient length for introduction into the patient and for manipulation from the point of insertion to the specific desired location within the heart. Merged with the distal end of the first section of the guiding introducer is the second section which is comprised of a curved portion followed by a straight portion, wherein the curved portion curves with a radius of about 0.2 in. (0.5 cm.) to about 0.5 in. (1.3 cm.) and preferably from about 0.3 in. (0.7 cm.) to about 0.4 in. (1.0 cm.) with an arc of about 50° to about 90°, preferably from about 60° to about 80°. The straight portion is from about 0.2 in. (0.5 cm.) to about 0.7 in. (1.8 cm.) in length and preferably about 0.4 in. (1.0 cm.) to about 0.5 in. (1.3 cm.) ending in the distal tip of the outer guiding introducer. Preferably, the first and second sections are generally coplanar (within about 15° of coplanar).

Figure 14A:
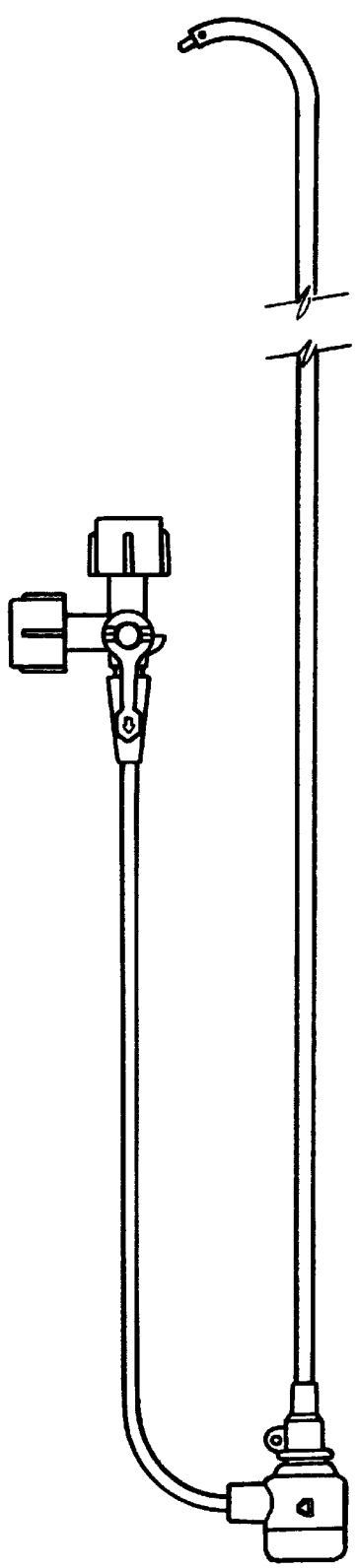
FIG. 14A is a first view of the inner guiding introducer for use in the left atrium as part of an alternative guiding introducer system to produce the tracks shown in FIGS. 3C and 3D defined as tracks 3 and 4, wherein the side port, which is attached to the proximal end of the guiding introducer, is directed to the left of the guiding introducer, but generally in the same plane thereof.
Figure 14B:
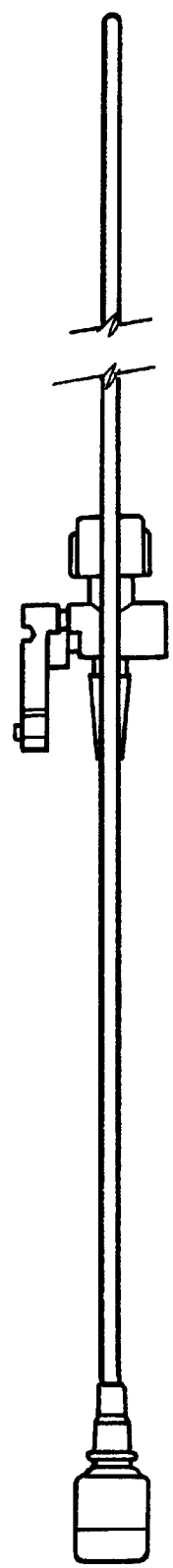
FIG. 14B is a second view of the inner guiding introducer for use in the left atrium as shown in FIG. 14A rotated 90° clockwise from the position of FIG. 14A such that the side port is directed behind the first section of the inner guiding introducer.

In a further alternative embodiment, the outer guiding introducer as shown in FIGS. 16A and 16B is utilized with the inner guiding introducer disclosed in FIGS. 14A and 14B to guide an ablation catheter to perform ablation procedures throughout the left atrium of the heart.

Although specific embodiments set forth herein describe "first," "second" and "third" sections, the present invention is not limited to such nomenclature or embodiments. For example, in general, the first section comprises an elongated section adapted to extend from an entry point to a location in the patient's inferior vena cava (IVC) or right atrium (RA) of the heart. The "second" section generally comprises a left atrium section which extends from the elongated section through the interatrial septum usually through the fossa ovalis into the left atrium of the patient's heart and terminates at a location therein. Finally, the "third" section may more generally be described as the trajectory section and extends from a left atrium section in a direction and at a relative angle to provide a desired trajectory to a catheter carried therein. Those skilled in the art will recognize that the elongated section, left atrium section and trajectory section may blend together and are not limited to specific junctions, shapes, angles, etc. These sections are not limited to the specific embodiments set forth herein and may be adapted as desired to achieve conformance with a particular physiology or other constraints which may be desirable or otherwise placed on the design. The elongated, left atrium and trajectory sections are related and intended to operate in concert to direct a catheter from the entry point in the patient to a desired trajectory on the atrial wall of the left atrium of a patient. Thus, the present invention includes all variations on the shapes, dimensions, angles, number of sections, etc. which are used in the guiding introducer system to achieve a desired trajectory.

The outer guiding introducer (100) as shown in FIGS. 16A and 16B is divided into at least two sections. The elongated or first section (hereinafter first section) (102) of the outer guiding introducer is a conventional, generally elongated straight introducer section of sufficient length for introduction into the patient and for manipulation from the point of insertion to the specific desired location within the heart. Merged with the distal end of the first section (102) of the guiding introducer (100) is the left atrium or second section (hereinafter second section) (104) which is comprised of a curved portion. The curved portion comprises an arc with a radius and a curvature. The radius of the arc is from about 0.5 in. (1.3 cm.) to about 2.0 in. (3.0 cm.), preferably about 1.0 in. (2.5 cm.) to about 1.5 in. (3.8 cm.), and the curvature of the arc is from about 90° to about 180°, preferably from about 110° to about 150°. Merged with the distal end of the second section is the trajectory or third section (hereinafter third section) (106) which comprises a straight section up to about 4.0 in. (10.1 cm.) in length, preferably less than about 0.5 in. (1.3 cm.), ending in the distal tip of the introducer. While FIGS. 16A and 16B show a third section (106), guiding introducer (100) may alternatively not include third section (106). If no third section (106) is used, the outer guiding introducer (100) ends with a distal tip at the end of the second section (104).

Figure 18A:
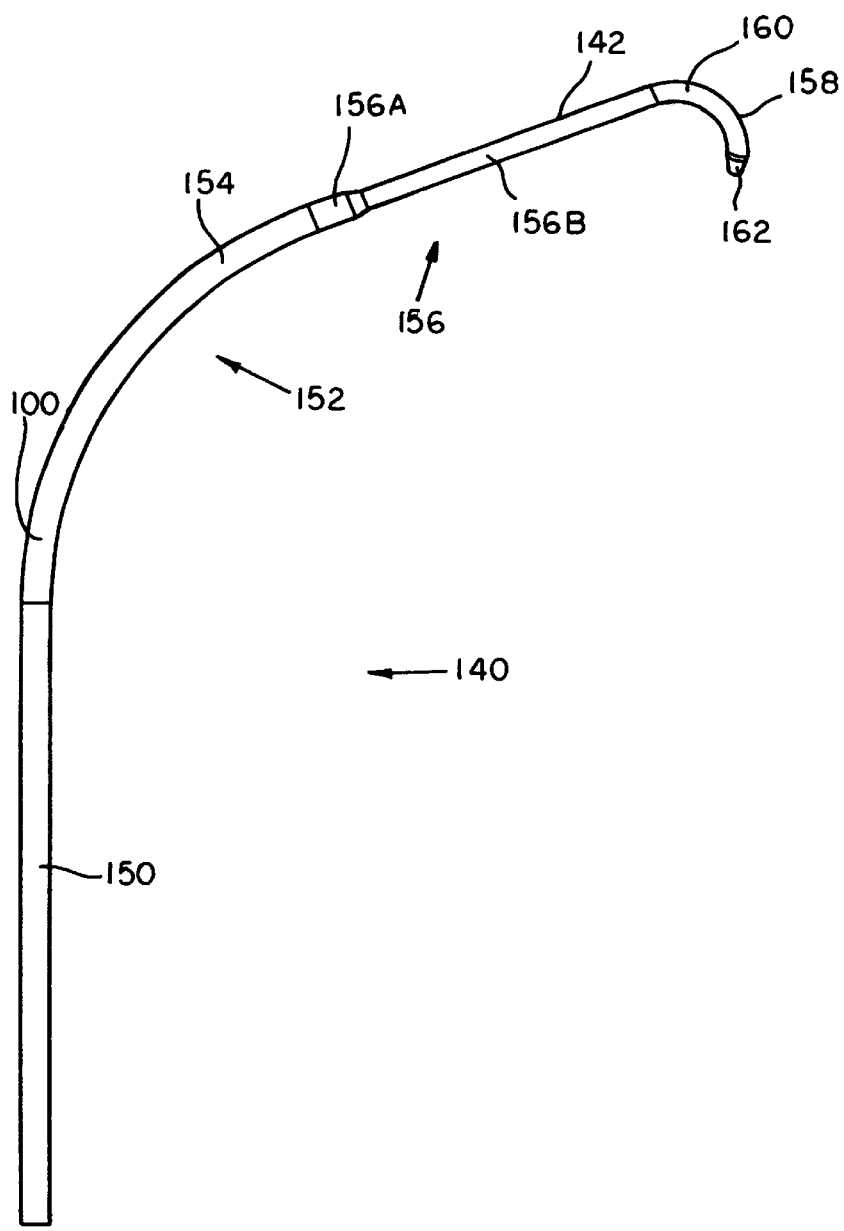
FIG. 18A is a side view of the outer guiding introducer disclosed in FIGS. 16A and 16B utilized in combination with the inner guiding introducer as shown in FIGS. 14A and 14B, wherein the curved portion of the inner guiding introducer is extended from a distal end of the outer guiding introducer.
Figure 18B:
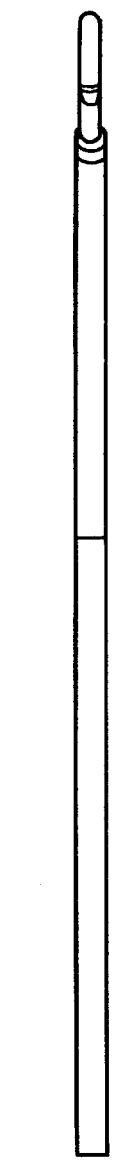
FIG. 18B is a front view of the combination of outer guiding introducer and inner guiding introducer as shown in FIG. 18A rotated 90° clockwise from its position in FIG. 18A.

The overall shape of the combination shape of the inner guiding introducer of FIGS. 14A and 14B with the outer guiding introducer of FIGS. 16A and 16B is shown in FIGS. 18A and 18B. This combination system (140) has a particular shape when the curved portion at the distal end of the inner guiding introducer of FIGS. 14A and 14B is extended from the distal tip of the outer guiding introducer (100) of FIGS. 16A and 16B. FIGS. 18A and 18B show the combination system in one plane. When the inner guiding introducer (142) is rotated (by an angular amount to achieve a desired trajectory of the ablation catheter) relative to the outer guiding introducer (100), the combined curve is three dimensional.

This shape of the combination of the inner and the outer guiding introducer (140) comprises a first, second and an optional third section. The elongated or first section (150) is a conventional, generally elongated straight introducer section of sufficient length for introduction into the patient and for manipulation from the point of insertion to the specific desired location within the heart. Merged with the distal end of the first section (150) of the combination of the inner and outer guiding introducers (140) is the left atrium or second section (152) which is comprised of a curved portion (154) and optional straight portions (156a) and (156b). The curved portion (154) comprises an arc with a radius and a curvature, wherein the radius of the arc is from about 1.5 in. (3.8 cm.) to about 4.0 in. (10.2 cm.), preferably from about 2.0 in. (5.0 cm.) to about 3.0 in. (7.6 cm.) in length. The curvature of the arc is from about 45° to about 90°, preferably from about 60° to about 80°. The straight portion (156) of this second section (152) may comprise portions 156a, 156b, or neither, and is up to about 8.0 in. (20.3 cm.), preferably 4.0 in. (10.1 cm.), and more preferably 2.0 in. (5.1 cm.) to 3.0 in. (7.6 cm.) in length. The trajectory or third section (158) of the combination of inner and outer guiding introducers (140) comprises a curved portion (160) and an optional straight portion (162). The curved portion (160) comprises an arc with a radius and a curvature. The radius of the arc is from about 0.1 in. (0.2 cm.) to about 1.0 in. (2.5 cm.), preferably from about 0.2 in. (0.5 cm.) to about 0.6 in. (1.5 cm.). The curvature of this arc is from about 60° to about 150°, preferably from about 100° to about 140°. The optional straight portion (162) of this third section is up to about 0.25 in. (0.7 cm.) in length. While FIGS. 18A and 18B show introducer system (140) with straight portions 156a, 156b, and 162, one or all of these portions need not be included.

As a further alternative embodiment, instead of utilizing the precurved inner guiding introducer shown in FIGS. 14A and 14B, a straight, uncurved inner guiding introducer can be utilized as shown in FIGS. 20A and 20B. This combination can be utilized to approach locations in the left atrium which are more difficult to approach utilizing the curved distal end of the guiding introducer shown in FIGS. 14A and 14B. The overall curvature and configuration of the combination of the precurved guiding introducer as shown in FIGS. 16A and 16B and the straight introducer (151) is similar to that discussed above, except that section (156) of the combination as shown in FIGS. 18A and 18B is straight and is referred to in this embodiment as the third section.

Figures 17A, 17B:
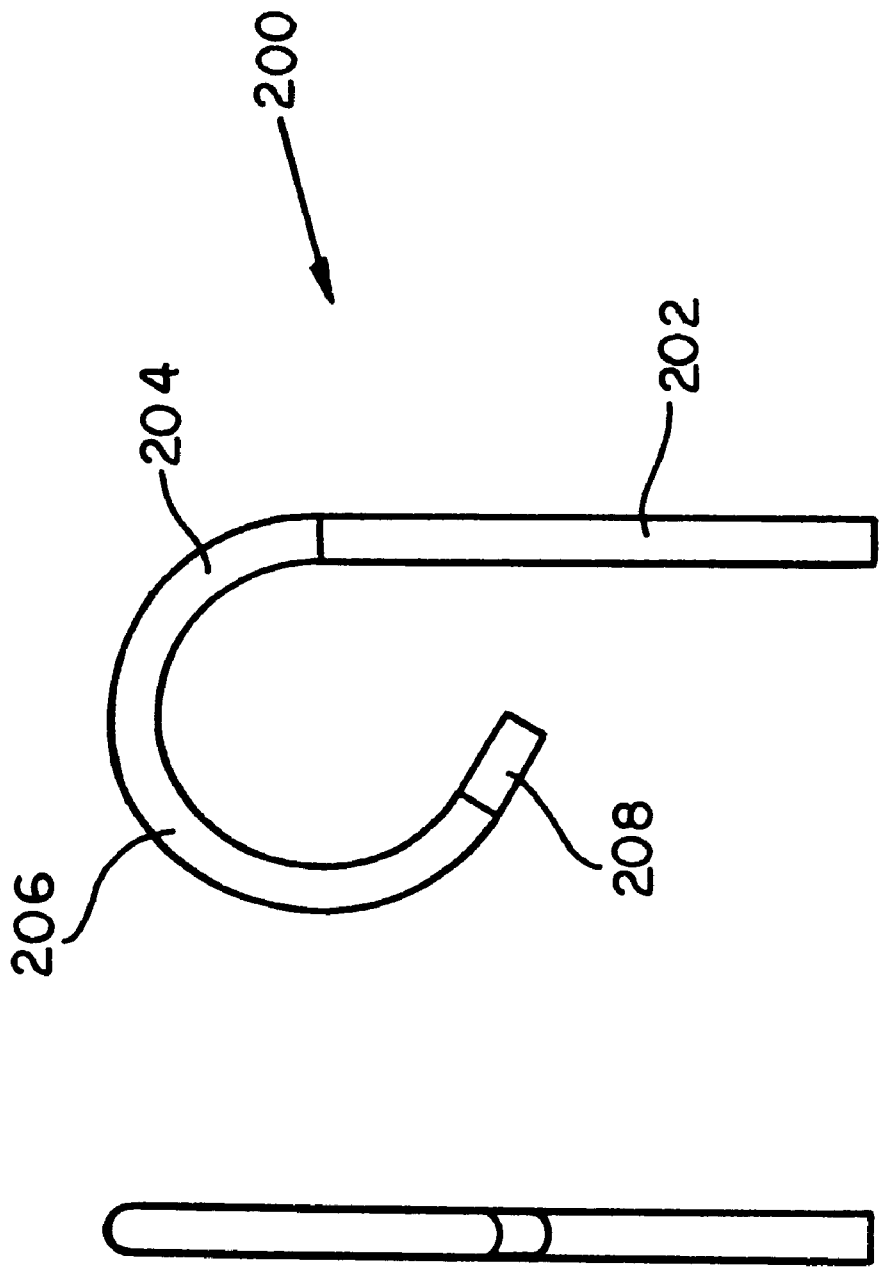
FIG. 17A is a side view of another outer guiding introducer for use in the left atrium as part of an alternative guiding introducer system.
FIG. 17B is a front view of the outer guiding introducer for use in the left atrium as shown in FIG. 17A rotated 90° clockwise from the position of FIG. 17A.

In a further alternative embodiment, the outer guiding introducer (200) as shown in FIGS. 17A and 17B is utilized with the inner guiding introducer disclosed in FIGS. 14A and 14B to guide an ablation catheter to perform ablation procedures throughout the left atrium of the heart.

The outer guiding introducer (200) of this alternative embodiment as shown in FIGS. 17A and 17B is divided into at least two sections. The elongated or first section (202) of the outer guiding introducer (200) is a conventional, generally elongated straight introducer section of sufficient length for introduction into the patient and for manipulation from the point of insertion to the specific desired location within the heart. Merged with the distal end of the first section (202) of the guiding introducer (200) is the left atrium or second section (204) which is comprised of a curved portion (206). The curved portion (206) comprises an arc with a radius and a curvature. The radius of the arc is from about 0.3 in. (0.7 cm.) to about 1.2 in. (3.1 cm.), preferably from about 0.5 in. (1.2 cm.) to about 0.75 in. (1.9 cm.) in length, and the curvature of the arc is from about 180° to about 300°, preferably from about 220° to about 260°. Merged with the distal end of the second section (204) is an optional trajectory or third section (208) which comprises a generally straight section up to about 4.0 in. (10.1 cm.), preferably less than about 0.5 in. (1.3 cm.) in length, ending in the distal tip of the introducer. While FIGS. 17A and 17B show third section (208) on outer guiding introducer (200), third section (208) need not be included. In this case, the distal tip would be at the end of the second section (204).

The overall shape of the combination of the inner guiding introducer of FIGS. 14A and 14B with the outer guiding introducer of FIGS. 17A and 17B is shown in FIGS. 19A and 19B. This combination system (250) has a particular shape when the curved portion at the distal end of the inner guiding introducer of FIGS. 14A and 14B is extended from the distal tip of the outer guiding introducer (200) of FIGS. 17A and 17B. FIGS. 19A and 19B show the combination system in one plane. When the inner guiding introducer (251) is rotated (by an angular amount to achieve a desired trajectory of the ablation catheter) relative to the outer guiding introducer, the combined curve is three dimensional.

The shape of the combination of the inner and the outer guiding introducer (250) comprises a first, second and optional third section. The elongated or first section (252) is a conventional, generally elongated straight introducer section of sufficient length for introduction into the patient and for manipulation from the point of insertion to the specific desired location within the heart. Merged with the distal end of the first section (252) of the combination of the inner and outer guiding introducers (250) is the left atrium or second section (254) which is comprised of a curved portion (256) and optional straight portions (258a) and (258b). The curved portion (256) comprises an arc with a radius and a curvature. The radius of the arc is from about 0.6 in. (1.5 cm.) to about 3.0 in. (7.7 cm.), preferably from about 1.2 in. (3.0 cm.) to about 2.0 in. (5.1 cm.). The curvature of the arc is from about 60° to about 130°, preferably from about 80° to about 110°. The optional straight portion (258), which may comprise both sections (258a) and (258b) or neither, of this second section (254) is up to about 8.0 in. (20.3 cm.), preferably 4.0 in. (10.1 cm.) and more preferably 2.0 in. (5.1 cm.)–3.0 in. (7.6 cm.) in length. The trajectory or third section (260) of the combination of guiding introducers (250) comprises a curved portion (262) and an optional straight portion (264). The curved portion (262) comprises an arc with a radius and a curvature. The radius of the arc is from about 0.1 in. (0.2 cm.) to about 1.0 in. (2.5 cm.) and preferably from about 0.2 in. (0.5 cm.) to about 0.6 in. (1.5 cm.). The curvature of this arc is from about 60° to about 150°, preferably from about 100° to about 140°. The optional straight portion (264) of this third section (260) is up to about 0.25 in.(0.6 cm.) in length. While FIGS. 19A and 19B show introducer system (250) with straight portions 258a, 258b, and 264, one or all of these portions need not be included.

Figure 21A:
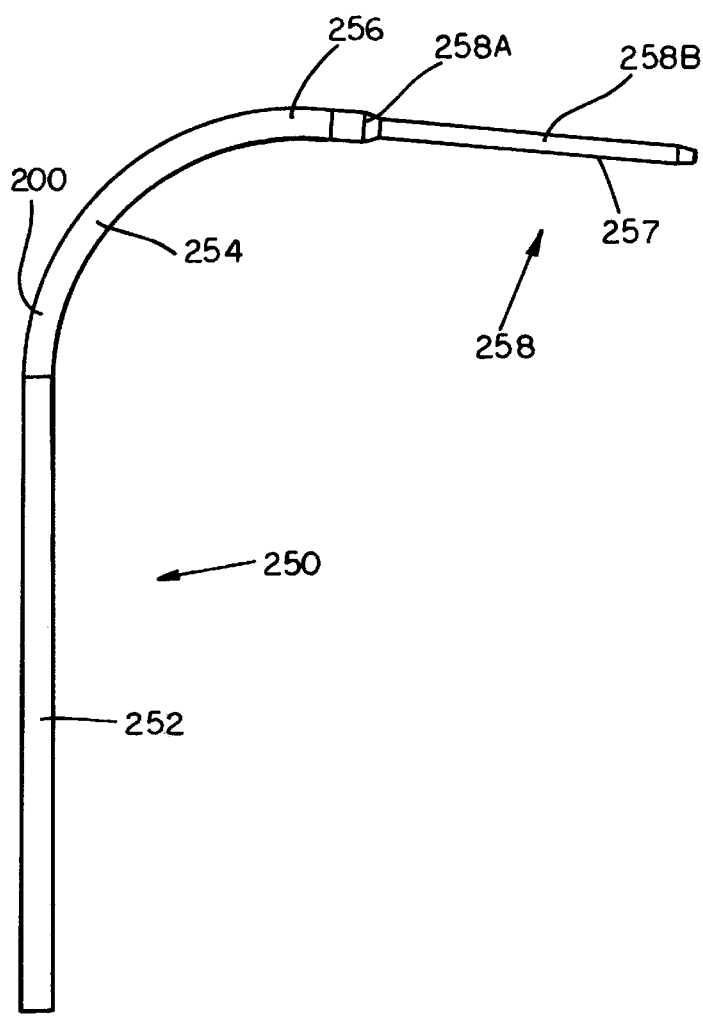
FIG. 21A is a side view of the outer guiding introducer disclosed in FIGS. 17A and 17B utilized in combination with a straight, uncurved inner guiding introducer, wherein a portion of the inner guiding introducer is extended from a distal end of the outer guiding introducer.
Figure 21B:
FIG. 21B is a front view of the combination of the outer guiding introducer and inner guiding introducer as shown in FIG. 21A rotated 90° clockwise from its position in FIG. 21A.

As a further alternative embodiment, a straight, uncurved guiding introducer can be substituted for the inner guiding introducer of the above-referenced combination such that the outer guiding introducer (200), as shown in FIGS. 17A and 17B, is utilized with the straight guiding introducer (257). This combination is shown in FIGS. 21A and 21B. This combination can be utilized to approach locations in the left atrium which are more difficult to approach utilizing the curved distal end of the guiding introducer. The overall curvature and configuration of this combination is the same as is shown in FIGS. 19A and 19B, except that the section (258) is straight and is referred to as the third section in this embodiment.

By extending or withdrawing the distal tip of the inner guiding introducer away from the distal tip of the outer guiding introducer a variety of shapes of the overall guiding introducer system are formed. These shapes permit significant modifications to the shape of guiding introducer system to permit an ablation catheter to ablate different locations by minor adjustments to the extension and/or rotation of the inner guiding introducer within the outer guiding introducer. A medical practitioner is able to view the relative location of the inner and outer guiding introducers because of tip markers located near the distal tip of both the inner and outer guiding introducers.

The relative size of the outer guiding introducer in relation to the inner guiding introducer should be sufficient to permit the inner guiding introducer to be torqued or rotated within the outer guiding introducer without undue restriction on such movement. Preferably, the difference in size between the inner and outer guiding introducer should be at least about 3 "French" (1 French equals one-third of a millimeter). For example in one preferred embodiment, the outer guiding introducer is 11 French in size and the inner guiding introducer is 8 French. By this difference in diameter, there is approximately 1 French unit of volume available between the outer surface of the inner guiding introducer and the inner surface of the outer guiding introducer. Preferably, this volume of space between the inner and outer guiding introducer is filled with a biocompatible solution, such as a saline solution, preferably a heparinized saline solution. This saline solution also provides lubricity to the two guiding introducers, allowing more accurate torquing of the inner guiding introducer within the outer guiding introducer. In addition, it is preferable that the structure of both the inner and the outer guiding introducer have a high torsional constant to allow for the full utilization of the various shapes available by rotation and extension of the inner and outer guiding introducer. To permit this high torsional constant, in one embodiment the inner guiding introducer is braided to provide further strength and structural stability.

The distal tip of all guiding introducers may be, and preferably will be, tapered to form a good transition with a dilator. This tapering is preferably less than 10° and more preferably about 4° to about 7°. The guiding introducers preferably may also contain one or a multitude of radiopaque tip marker bands near the distal tip of the introducer. These guiding introducers also preferably contain one or a plurality of vents near the distal tip of the guiding introducer, preferably three or four such vents. The vents are preferably located no more than about 1.00 in. (2.5 cm.) from the tip of the guiding introducer and more preferably 0.10 in. (0.25 cm.) to about 1.00 in. (2.5 cm.) from the tip. The size of these vents should be in the range of about 40 to about 60/1000 of an inch in diameter. These vents are generally designed to prevent air embolisms from entering the guiding introducer caused by the withdrawal of the catheter contained within the guiding introducer in the event the distal end of the guiding introducer is occluded. For example, if the tip of the guiding introducer is placed against the myocardium and the catheter located within the guiding introducer is withdrawn, a vacuum may be created within the catheter if no vents are provided. If such vacuum is formed, air may be forced back into the guiding introducer by the reintroduction of the catheter into the lumen of the guiding introducer. Such air embolisms could cause significant problems in the patient, including the possibility of a stroke, heart attack or other such problems common with air embolisms in the heart. The addition of vents near the distal tip of the guiding introducer prevents the formation of such vacuum by permitting fluid, presumably blood, to be drawn into the lumen of the guiding introducer as the catheter is being removed from the guiding introducer, thus preventing the possibility of formation of air embolisms within the guiding introducer.

The guiding introducers may be made of any material suitable for use in humans which has a memory or permits distortion from, and substantial return to, the desired three dimensional or complex multiplanar shape. For the purpose of illustration and not limitation, the internal diameter of the guiding introducers may vary from about 6 to about 12 "French" (1 French equals ⅓ of a millimeter). Such guiding introducer can accept dilators from about 6 to about 12 French and appropriate guidewires. Obviously, if larger or smaller dilators or catheters are used in conjunction with the guiding introducers of the instant invention, modifications in size or shape can be made to the instant guiding introducers.

Variations in size and shape of the guiding introducers are also intended to encompass pediatric uses for the guiding introducers of the instant invention, although the preferred uses are for adult human hearts. It is well recognized that pediatric uses may require reductions in size of the various sections of the guiding introducers, in particular the first section, but without any significant modification to the shape or curve of the guiding introducers.

In addition, variations in size or shape of the guiding introducers are also intended to encompass the specialized situations that sometimes occur in patients with enlarged and rotated hearts. The guiding introducer systems are especially useful with these enlarged and rotated hearts.

Figure 4B:
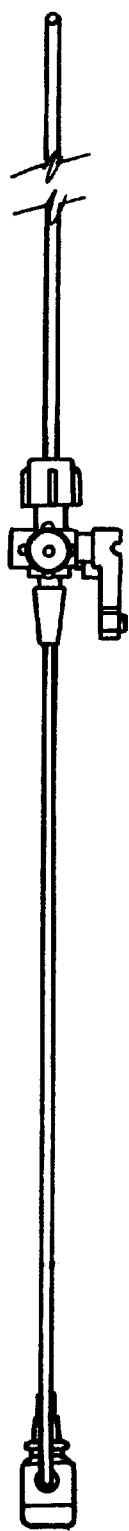
FIG. 4B is a second view of the first guiding introducer for the right atrium rotated 90° clockwise from the position of FIG. 4A such that the side port tubing is positioned over a portion of the first section of the first guiding introducer.
Figure 4A:
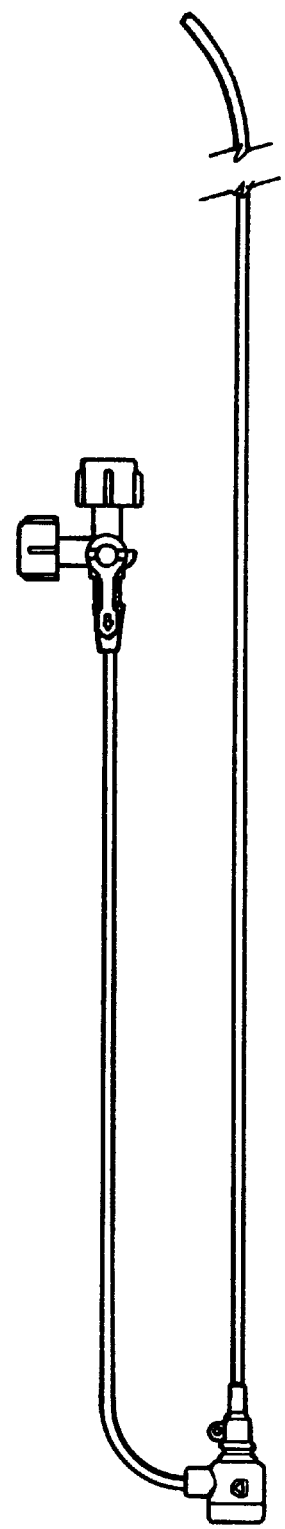
FIG. 4A is a first view of the first guiding introducer for the right atrium as used in FIGS. 3G, 3I and 3J to produce track 7 and track 8 in the right atrium with the side port tubing, which is attached to the proximal end of the guiding introducer, directly to the left of the guiding introducer but generally in the same plane thereof.
Figure 5B:
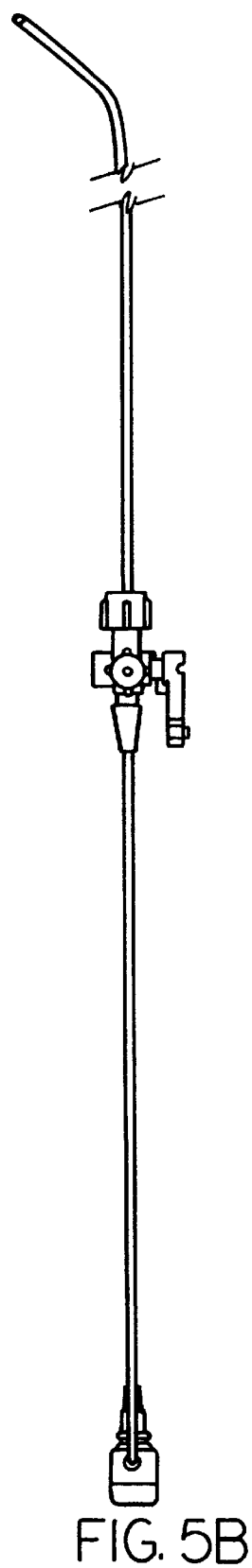
FIG. 5B is a second view of the second guiding introducer for the right atrium of FIG. 5A wherein the guiding introducer is rotated 90° clockwise from the position of FIG. 5A such that the side port tubing is positioned over a portion of the first section of the second guiding introducer.
Figure 5A:
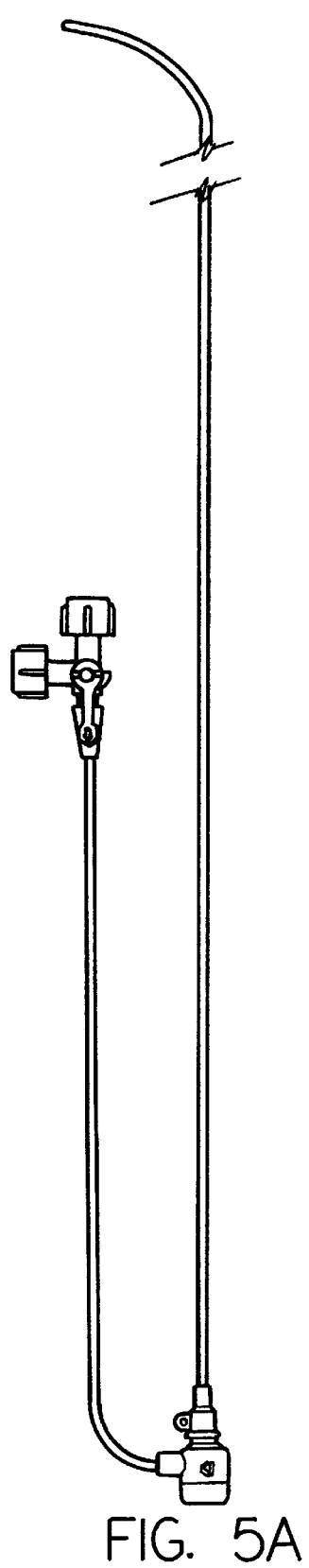
FIG. 5A is a first view of the second guiding introducer for the right atrium for use as shown in FIG. 3E to produce track 5 with the side port tubing, which is attached to the proximal end of the guiding introducer, directly to the left of the guiding introducer but generally in the same plane thereof.

The second guiding introducer for use in the right atrium is shown in FIGS. 5A and 5B. This is the same shaped guiding introducer shown in FIG. 4 in pending application Ser. No. 08/147,168, assigned to a common assignee. It is designed to ablate the isthmus of tissue separating the tricuspid valve from the inferior vena cava. See FIG. 2, track 5 and FIG. 3E. Once this ablation is complete, reentry circuits are prevented from forming around the tricuspid valve or the superior and inferior vena cava. This guiding introducer is also divided into three sections. The first section is a conventional generally elongated hollow straight introducer section of sufficient length for introduction into the patient and for manipulation from the point of insertion to the specific desired location within the heart. Merged with the distal end of the first section of the guiding introducer is the second section which is curved in a compound curve curving first upward in a first curve as shown in FIG. 5B and simultaneously curving to the left in a second curve. The first longitudinal curve has a radius of from about 0.50 in. (1.2 cm.) to about 2.00 in. (5.1 cm.) and preferably from about 0.50 in. (1.2 cm.) to about 1.50 in. (3.8 cm.). The inner angle of the first longitudinal curve is preferably from about 140° to about 120° and preferably from about 135° to about 125°. The second longitudinal curve of the second section contains a radius from about 0.50 in. (1.2 cm.) to about 4.00 in. (10.1 cm.) and preferably from about 0.50 in. (1.2 cm.) to about 2.00 in. (5.1 cm.). The angle of the second longitudinal curve is preferably to the left as shown on FIG. 5A from about 70° to about 110° and preferably from about 80° to about 100°. The third section of the guiding introducer is merged with the distal end of the second section. The third section is a third curved section wherein the plane of the third section is angled upward at an angle of approximately 40° to about 60° and more preferably about 45° to about 55° from the plane of the first section wherein substantially all of the third section is coplanar. See FIGS. 5A and 5B. The arc of the curve of this third section has a radius of about 80° to about 100° and preferably from about 85° to about 95°.

Figure 6C:
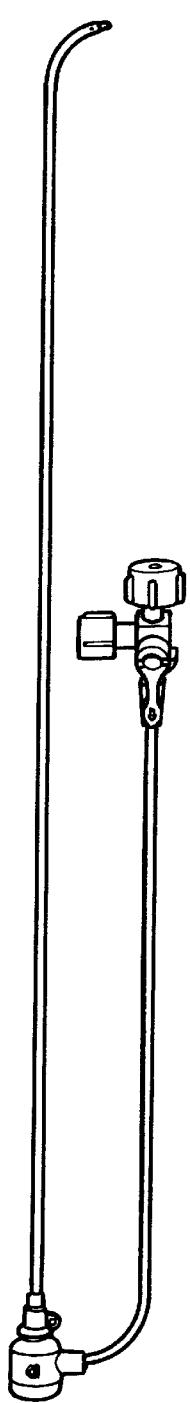
FIG. 6C is a third view of the third guiding introducer for the right atrium of FIG. 6A rotated 180° from the position of FIG. 6A such that the side port tubing is directly to the right of the guiding introducer but generally in the same plane thereof.
Figure 6B:
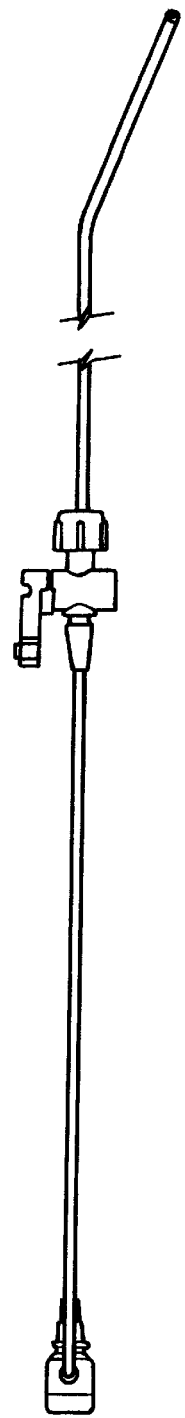
FIG. 6B is a second view of the third guiding introducer for the right atrium of FIG. 6A wherein the guiding introducer is rotated 90° clockwise from the position of FIG. 6B such that the side port tubing is positioned on top of a portion of the first section of the third guiding introducer.
Figure 6A:
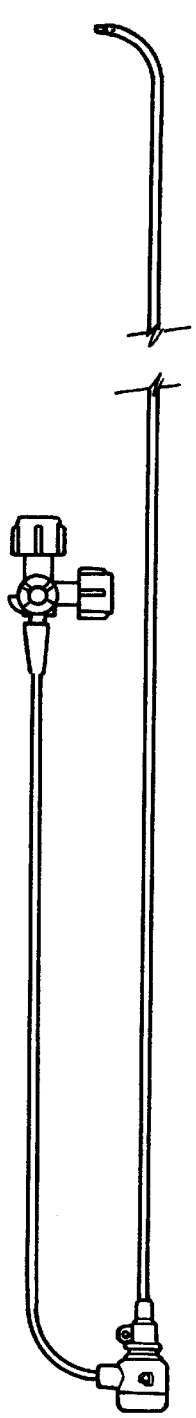
FIG. 6A is a first view of the third guiding introducer for the right atrium for use as shown in FIGS. 3F, 3G and 3H to produce tracks 6, 7 and 9 with the side port tubing, which is attached to the proximal end of the guiding introducer, directly to the left of the guiding introducer but generally in the same plane thereof.

The third ablation track in the right atrium runs along the crista terminalis around the superior and inferior vena cava. See FIG. 1, track 6 and FIG. 3F. Along with the first track in the right atrium in FIG. 1, track 5, this track is designed to prevent the formation of reentry circuits around the superior and inferior vena cava. The third right side guiding introducer to produce this ablation track also has a preferred shape. This guiding introducer is divided into three sections as shown in FIGS. 6A, 6B and 6C. (Each of the remaining guiding introducers will also be shown in two or three different views. In each of the views the guiding introducers will be secured to a valve for attachment to a conventional catheter and stop cock. In each such arrangement, the shape of the guiding introducer will be described making reference to its position in relation to the side port tubing where the proximal end of the guiding introducer is secured in place.) In the first of these three figures, the side port is generally in the plane of the first straight section of the guiding introducer but directed 90° to the left (see FIG. 6A). In the second drawing, the side port is rotated 90° clockwise such that the stop cock and the remaining portion of the tubing appear to cover a portion of the first section of the guiding introducer (see FIG. 6B). The third drawing (FIG. 6C) rotates the side port tubing 90° further clockwise, such that it is once again generally in the same plane as the first section of the guiding introducer but with the side port tubing on the right side of the drawing. See FIG. 6C. (Similar arrangements of the guiding introducers with the side port tubing are used with the remaining guiding introducers to assist in description.)

The first section of the third guiding introducer for the right atrium is a conventional, generally elongated hollow straight introducer section of sufficient length for introduction into the patient and for manipulation from the point of insertion to the specific desired location within the right atrium of the heart. Merged with the distal end of the first section of the second shaped, guiding introducer is a second section which is comprised of a curved section, curving to the right as shown in FIG. 6B. The inner angle of this curve is from about 170° to about 150° and preferably from about 165° to about 150°. The radius of the curve is from about 1.50 in (3.8 cm.) to 2.00 in. (5.1 cm.) and preferably from about 1.65 in. (4.2 cm.) to about 1.85 in. (4.7 cm.). At the end of this curve begins the third section which is first a generally straight section of about 1.00 in. (2.5 cm.) to 1.60 in. (4.1 cm.) and preferably from about 1.25 in. (3.2 cm.) to about 1.40 in. (3.6 cm.) in length, concluding in a curve to the right as shown in FIG. 6C (or to the left in FIG. 6A) at an inner angle of about 70 to about 110° and preferably from about 80 to about 100°. The radius of this curve is from about 0.30 in. (0.8 cm.) to about 0.50 in. (1.3 cm.) and preferably from about 0.35 in. (0.9 cm.) to about 0.40 in. (1.0 cm.). At the end of this curve is the distal tip of the guiding introducer. Preferably the overall length of this third section of the third section beginning at the curve and extending to the distal tip is from about 0.40 in. (1.0 cm.) to about 0.70 in. (1.8 cm.) and more preferably from about 0.50 in. (1.3 cm.) to about 0.60 in. (1.5 cm.). The distal tip of this guiding introducer may and preferably will be tapered to form a good transition with a dilator. In addition, tip markers and vents may be provided and preferably are provided near the distal tip of the guiding introducer as has been previously described.

Two additional tracks are produced in the right atrium. These are designated as tracks 7 and 9 on FIG. 1. Track 7 runs along the atrio-septal wall between the medial aspect of the superior vena cava and the inferior vena cava. This track assists in preventing the formation of reentry circuits around the superior and inferior vena cavas. The last track runs from the medial aspect of the superior vena cava near the end of the track made near the crista terminalis running anterior to the tip of the right atrial appendage. This track assists in preventing the formation of reentry circuit around the right atrial appendage. Both of these tracks can be produced either by using the first guiding introducer for the right atrium which is used to produce track 8 as shown in FIGS. 4A and 4B or the third guiding introducer for the right atrium which is used to produce the crista terminalis track designated as 6 on FIG. 1 as shown in FIGS. 6A, 6B and 6C. No additional description of these guiding introducers is necessary.

The guiding introducers for use in the left atrium will now be discussed in detail. The first guiding introducer or guiding introducer system for use in the left atrium is designed to isolate the left atrial appendage from the left pulmonary veins. Thus, the guiding introducer or introducer system is designed to assist the ablation catheter in the creation of an ablation track running from the mitral valve and the atrioventricular groove at a point anterior to the left pulmonary veins to the interatrial septum.

Figure 3A:
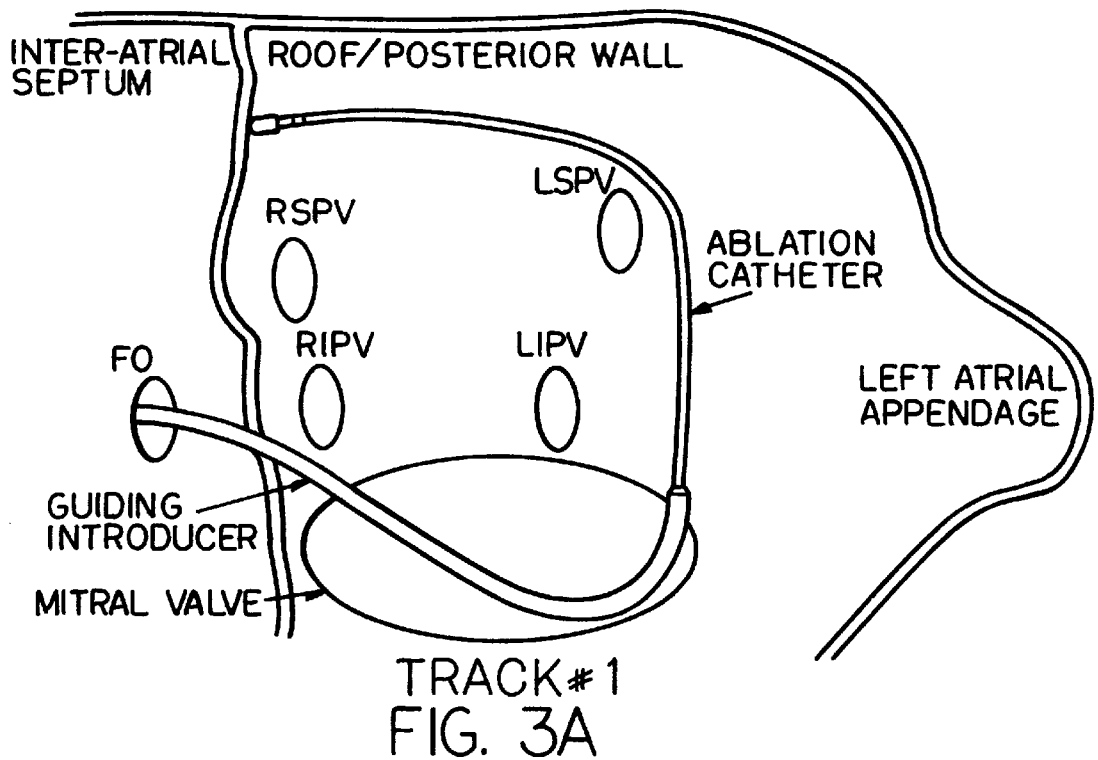
FIG. 3A is a schematic drawing of the left atrium showing the use of the first guiding introducer for the left atrium as shown in FIGS. 7A, B and C to produce track 1.

See FIG. 2, track 1 and FIG. 3A. While preferable, all four tracks are necessary for complete ablation of reentry circuits, it is possible that relief of atrial fibrillation in the left atrium may be achieved by ablation of only this first track.

The first guiding introducer for use in the left atrium is preferably the same guiding introducer used to produce ablation track 8 in the left atrium in the interatrial septum which corresponds with track 8 in the right atrium. See FIGS. 3I and 3K and FIGS. 7A, 7B and 7C. Alternatively, the guiding introducer system disclosed in FIGS. 12A and 12B and FIGS. 13A and 13B may also be used to ablate this track.

The second guiding introducer for the left atrium is used to isolate the left pulmonary veins from the right pulmonary veins.

Figure 3B:
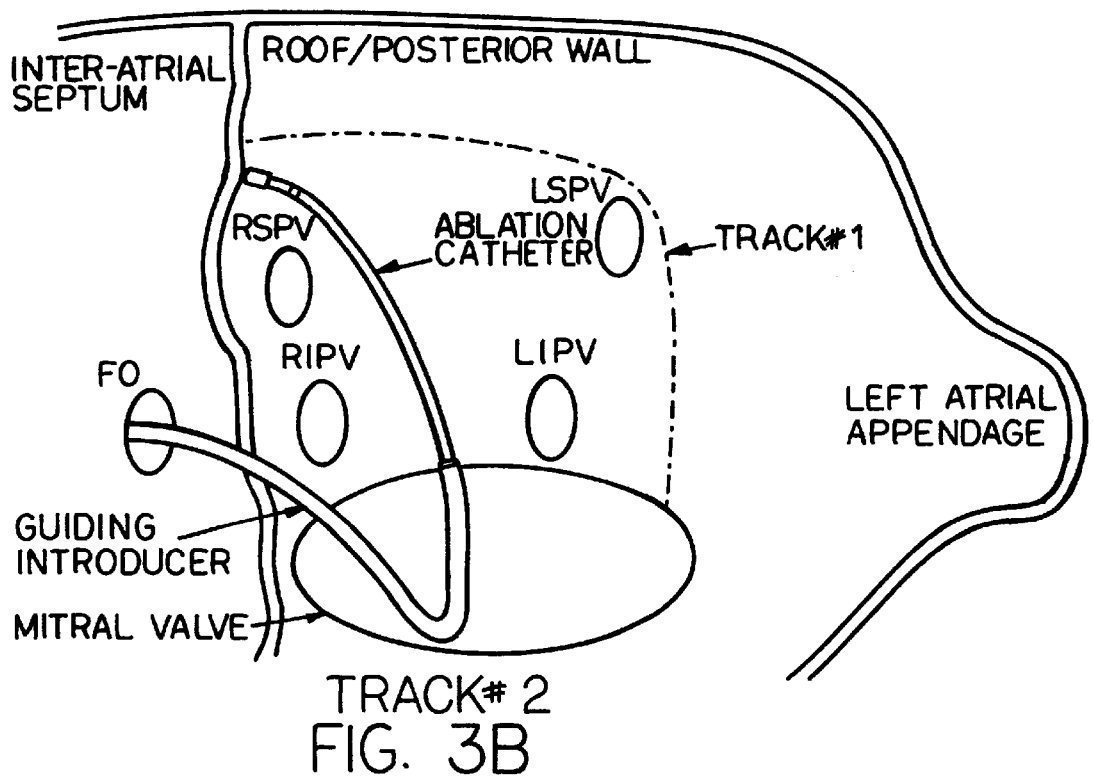
FIG. 3B is a schematic drawing of the left atrium showing the use of the second guiding introducer for the left atrium as shown in FIGS. 9A, B and C to produce track 2.
Figure 9C:
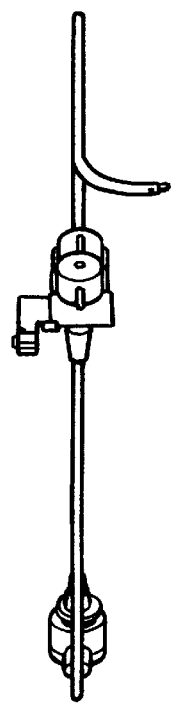
FIG. 9C is a third perspective view of the second guiding introducer for the left atrium rotated 180° from the position of FIG. 9B such that the side port tubing attached to the proximal end of the guiding introducer is positioned over a portion of the second guiding introducer for the left atrium.
Figure 9A:
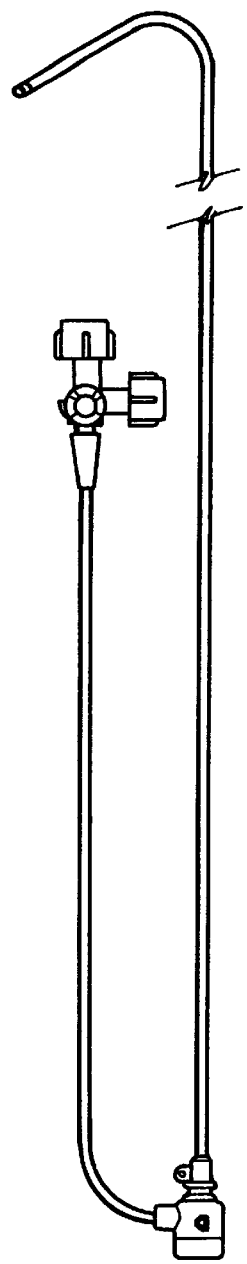
FIG. 9A is a first view of the second guiding introducer for the left atrium for use as shown in FIG. 3B to produce track 2 with the side port tubing, which is attached to the proximal end of the guiding introducer, directly to the left of the guiding introducer and generally in the same plane thereof.
Figure 9B:
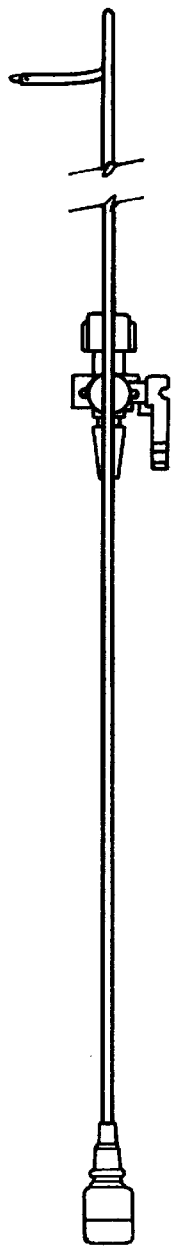
FIG. 9B is a second view of the second guiding introducer for the left atrium as shown in FIG. 9A rotated 90° counterclockwise such that the guiding introducer is positioned over the side port tubing.

See FIG. 2, track 2 and FIG. 3B. The ablation track created by use of the second guiding introducer is located roughly parallel to that of the track created by the first shaped, guiding introducer with the ablation catheter. The track runs from the mitral valve in the atrialventricular groove to the interatrial septum but between the right and left pulmonary veins. The shape of the second guiding introducer is similar to that of the first guiding introducer. The second guiding introducer is also divided into three sections. Referring now to FIGS. 9A, 9B and 9C for three views of the second guiding introducer, the first section is a conventional, generally elongated hollow, straight introducer section of sufficient length for introduction into the patient and for manipulation from the point of insertion to the specific desired location within the left atrium of the heart. Merged with the distal end of the first section of the first shaped, guiding introducer is a second section which is comprised of a curved section followed by a straight section. The curved section is curved to the left and downward when placed in the position shown in FIG. 9A. The inner angle of this curve is from about 40° to about 80° and more preferably from about 50 to about 70°. The radius of this curve is from about 0.30 in. (0.7 cm.) to about 0.50 in. (1.3 cm.) and preferably from about 0.35 in. (0.9 cm.) to about 0.40 in. (1.1 cm.). At the end of this curve is the straight section from about 0.50 in. (1.3 cm.) to about 1.00 in. (2.5 cm.) in length and preferably from about 0.70 in. (1.8 cm.) to about 0.80 in. (2.0 cm.). The third section of this second shaped, guiding introducer is merged with the distal end of the straight section of the second section. The third section is comprised of a curved section followed by a straight section. The curved section curves backward in relation to the first section when placed as shown in FIG. 9A and to the left as shown in FIG. 9B with the measure of the angle being about 80 to 100° and preferably from about 85 to 95° with a radius of about 0.25 in. (0.6 cm.) to about 0.40 in. (1.0 cm.) and preferably from about 0.30 in. (0.7 cm.) to about 0.40 in. (1.0 cm.). At the end of this curve is a short straight section whose length is from about 0.30 in. (0.7 cm.) to about 0.70 in. (1.8 cm.) and preferably from about 0.40 in (1.0 cm.) to about 0.60 in. (1.5 cm.), ending in the distal tip of the catheter. The distal tip of this second shaped, guiding introducer may be, and preferably will be, tapered to form a good transition with a dilator as with the first guiding introducer. In addition, tip markers and vents may be provided near the distal tip of the guiding introducer as has been previously described.

Alternatively, the guiding introducer system previously discussed as is disclosed in FIGS. 12A, 12B, 13A and 13B can also be used in place of the first and/or second guiding introducers previously described to produce track 2 in the left atrium as shown on FIG. 3B.

Figure 10B:
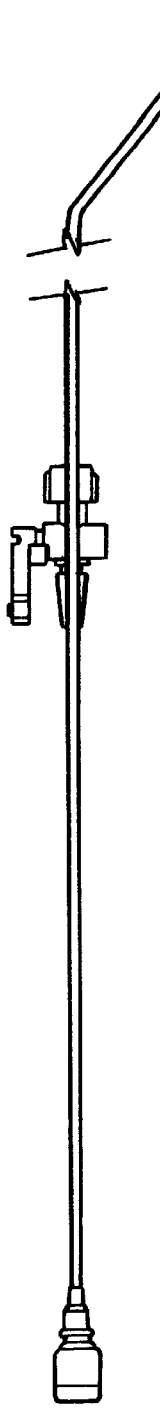
FIG. 10B is a second view of the third guiding introducer for the left atrium of FIG. 10A rotated 90° counterclockwise such that the side port tubing is behind the first section of the third guiding introducer.
Figure 10C:
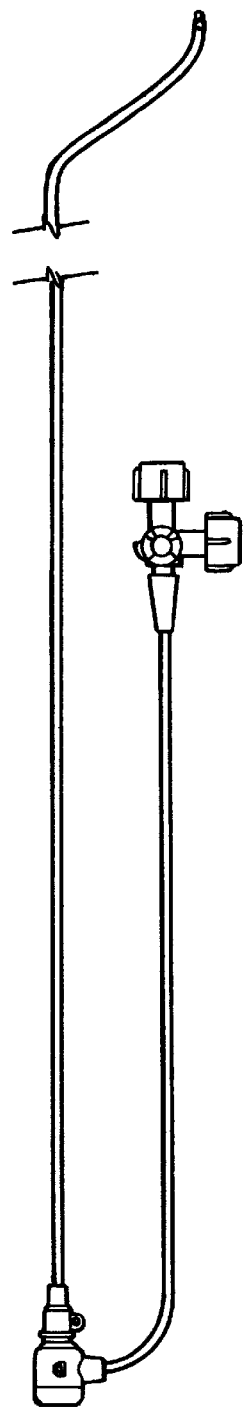
FIG. 10C is a third view of the third guiding introducer for the left atrium rotated 180° from the position shown in FIG. 10A with the side port tubing directly to the right of the guiding introducer and wherein the straight section of the third guiding catheter is generally in the same plane thereof.
Figure 10A:
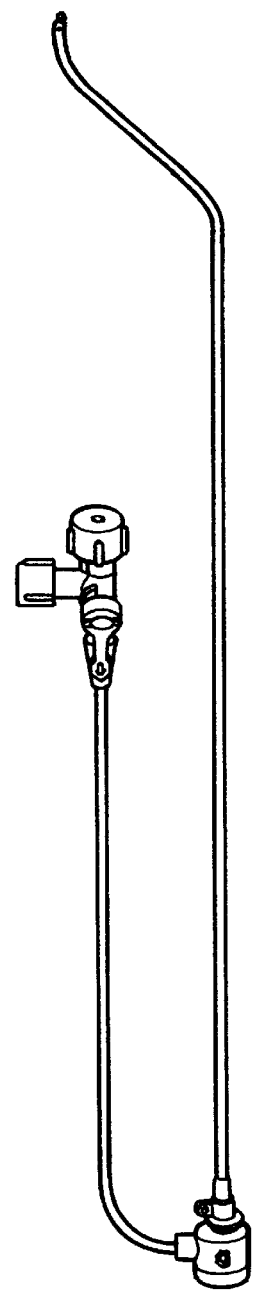
FIG. 10A is a first view of the third guiding introducer for the left atrium for use as shown in FIG. 3C to produce track 3 with the side port tubing, which is attached to the proximal end of the guiding introducer, directly to the left of the guiding introducer and generally in the same plane thereof.

Referring now to FIGS. 10A, 10B and 10C for three different views, the third guiding introducer for use in the left atrium has a significantly different shape than the first two individual guiding introducers for the left atrium. It is specifically designed to complete the isolation of the left interior pulmonary vein and surrounding tissue from the remaining portion of the left atrium. See FIG. 2, track 3 and FIG. 3C. It is designed to assist in the creation of an ablation track running from a point superior and lateral from the left inferior pulmonary vein and extends between the left pulmonary veins to intersect with the tracks created by the ablation catheters when used with the first and second guiding introducers for the left atrium.

The third guiding introducer is comprised of a first, second and third section. See FIGS. 10A, 10B and 10C. The first section of this third guiding introducer is a conventional generally elongated hollow, straight introducer section of sufficient length for introduction and for manipulation from the point of insertion to the specific desired location within the left atrium. Merged with the distal end of the first section is the second section which is comprised of a compound curve followed by a straight section. The compound curve of the second section is curved first to the left in a first curve in relation to the first straight section, as shown in FIG. 10A and simultaneously curving backward in relation to the first section in a second curve (or to the right as shown in FIG. 10B). The first curve has a radius of about 0.40 in. (1.0 cm.) to about 0.60 in. (1.5 cm.) and preferably from about 0.45 in. (1.1 cm.) to about 0.55 in. (1.4 cm.). The inner angle of the first curve is preferably from about 155° to about 115° and preferably from about 140° to about 120°. The second curve of this second section has a radius of about 0.15 in. (0.4 cm.) to about 0.45 in. (1.1 cm.) and preferably from about 0.20 in. (0.5 cm.) to about 0.30 in. (0.8 cm.). The inner angle of this second curve is from about 120° to about 160° and preferably from about 130° to about 150°. The straight portion of this second section of this third guiding introducer begins at the end of this compound curve and is about 1.20 in. (3.0 cm.) to about 1.50 in. (3.8 cm.) and preferably from about 1.30 in. (3.3 cm.) to about 1.50 in. (3.8 cm.) in length. At the end of this straight section begins the third section which is comprised of a curved section followed by a straight section. The curved section curves at an inner angle of about 155° to about 115°, preferably about 140° to about 120° as shown in FIG. 10A and has a radius of about 0.40 in. (1.0 cm.) to about 0.60 in. (1.5 cm.). This curve is in the same plane as the straight portion of the second section. At the end of this curve is the straight section ending in the distal tip of the guiding introducer. This straight section is relatively short, preferably about 0.20 in. (0.5 cm.) to about 0.40 in. (1.0 cm.). Preferably, it is tapered to form a good transition with a dilator. As with the other guiding introducers, radiopaque tip marker bands may be used as well as preferably vents near the distal tip.

The fourth guiding introducer for the left atrium is specifically designed for use in the left atrium to isolate the right inferior pulmonary vein from the right superior pulmonary vein. It is designed to assist in the creation of an ablation track running from the posterior aspect of the interatrial septum, anterior between the right superior and inferior pulmonary veins to intersect the second track. See FIG. 2, track 4 and FIG. 2D.

Figure 11B:
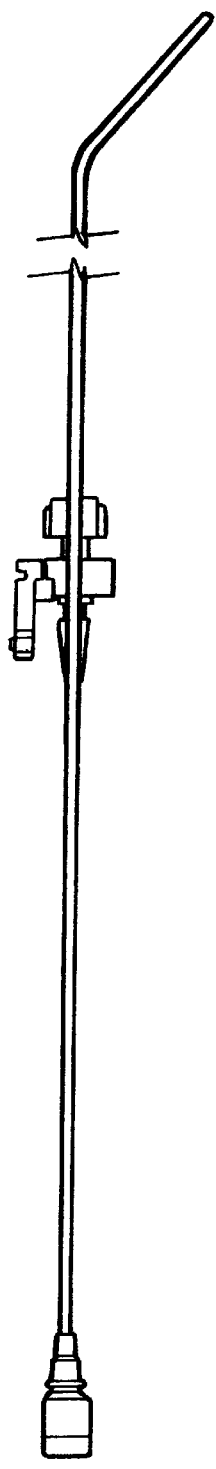
FIG. 11B is a second view of the fourth guiding introducer for the left atrium rotated 90° counterclockwise from the position of FIG. 11A such that the side port tubing is behind the first section of the fourth guiding introducer.
Figure 11C:
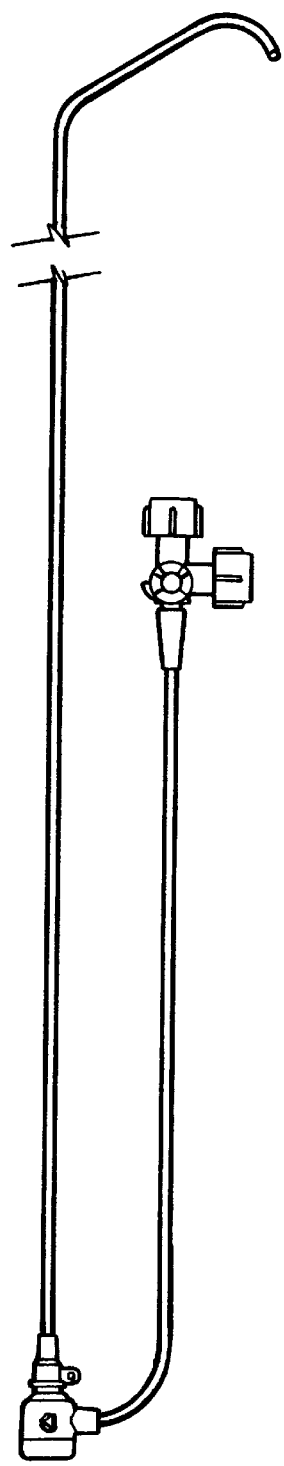
FIG. 11C is a third view of the fourth guiding introducer for the left atrium rotated 180° from the position shown in FIG. 11A with the side port tubing to the right of the guiding introducer and the straight section of the fourth guiding catheter generally in the same plane thereof.
Figure 11A:
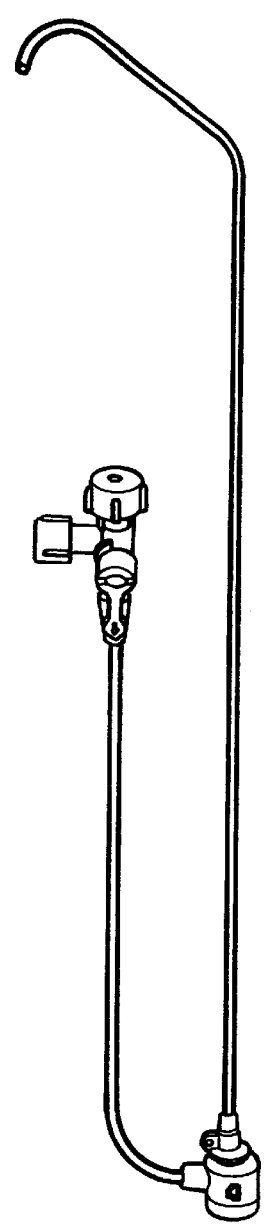
FIG. 11A is a first view of the fourth guiding introducer for the left atrium for use as shown in FIG. 3D to produce track 4 with the side port tubing, which is attached to the proximal end of the guiding introducer, directly to the left of the guiding introducer and generally in the same plane thereof.

The shape of the fourth guiding introducer is different from that of the first three guiding introducers for the left atrium and is comprised of a first, second and third sections. See FIGS. 11A, 11B and 11C for three different views. The first section is a conventional generally elongated hollow, straight introducer section of sufficient length for introduction into the patient and for manipulation from the point of insertion to the specific desired location within the left atrium. Merged with the distal end of this first section is the second section which is comprised of a compound curved section followed by a straight section. The compound curved section curves first to the left in relation to the first section as shown in FIG. 11A in a first curve and simultaneously curves backward away from the first section (or to the right as shown in FIG. 11B) in a second curve. The first curve has an inner angle of about 155° to about 105°, preferably from about 140° to about 120° with a radius of about 0.25 in. (0.6 cm.) to about 0.50 in. (1.3 cm.) and preferably from about 0.30 in. (0.7 cm.) to about 0.40 in. (1.0 cm.). The second curve has an inner angle of about 155° to about 125° and preferably from about 150° to about 130° with a radius of about 0.30 in. (0.7 cm.) to about 0.70 in. (1.8 cm.) and preferably from about 0.40 in. (1.0 cm.) to about 0.60 in. (1.5 cm.). At the end of the compound curved section of the second section is the straight section of the second section of the fourth guiding introducer which is from about 1.00 in. (2.5 cm.) to about 2.00 in. (5.0 cm.) and preferably from about 1.20 in. (3.0 cm.) to about 1.50 in. (3.8 cm.) in length. At the end of this straight section is the third section, which is comprised of a curved section ending in the distal tip of the guiding introducer. The curved section curves to the left in an arc from the plane of the first section as shown in FIG. 11A at an inner angle of about 40° to about 80° and preferably from about 50° to about 70° with a radius of about 0.30 in. (0.7 cm.) to about a 0.50 in. (1.3 cm.) and preferably from about 0.35 in. (0.9 cm.) to about 0.40 in. (1.0 cm.). As with the first, second and third guiding introducers for the left atrium, radiopaque tip marker bands may be used as well as preferably vents near the distal tip of the fourth guiding introducer.

Alternatively to the third and fourth guiding introducers for the left atrium which are used to ablate tracks 3 and 4, a second guiding introducer system comprised of a second inner and a second outer guiding introducer may be used to replace either or both of these guiding introducers. A transseptal dilator for use with cardiac procedures is used with the guiding introducer system. The dilator is generally curved at its distal end. Generally the last 5 to 15 in. at the distal end are curved. The radius of the curve is preferably about 2.5 in. (0.3 cm.) to about 4.0 in. (10.2 cm.) with an arc of about 20° to about 40° ending in a conventional distal tip. The standard length of the dilator is from about 60 to about 90 cm.

The second inner guiding introducer to produce tracks 3 and 4 on FIG. 2 is generally comprised of two sections. See FIGS. 14A and 14B. The first section is a conventional, generally elongated, hollow straight introducer section of sufficient length for introduction into the patient and for manipulation from the point of insertion to the specific desired location within the heart. Merged with the distal end of the first section of the guiding introducer, but an integral part of the inner guiding introducer, is the second section which is a curved section curving in a simple curve to the left as shown in FIG. 14A with a radius of about 0.2 in. (0.5 cm.) to about 0.5 in. (1.3 cm.) preferably from about 0.3 in. (0.7 cm.) to about 0.4 in. (1.0 cm.) to form an arc of about 100° to about 140° and preferably from about 110° to about 130° ending in the distal tip of the second inner guiding introducer.

Figures 15A, 15B:
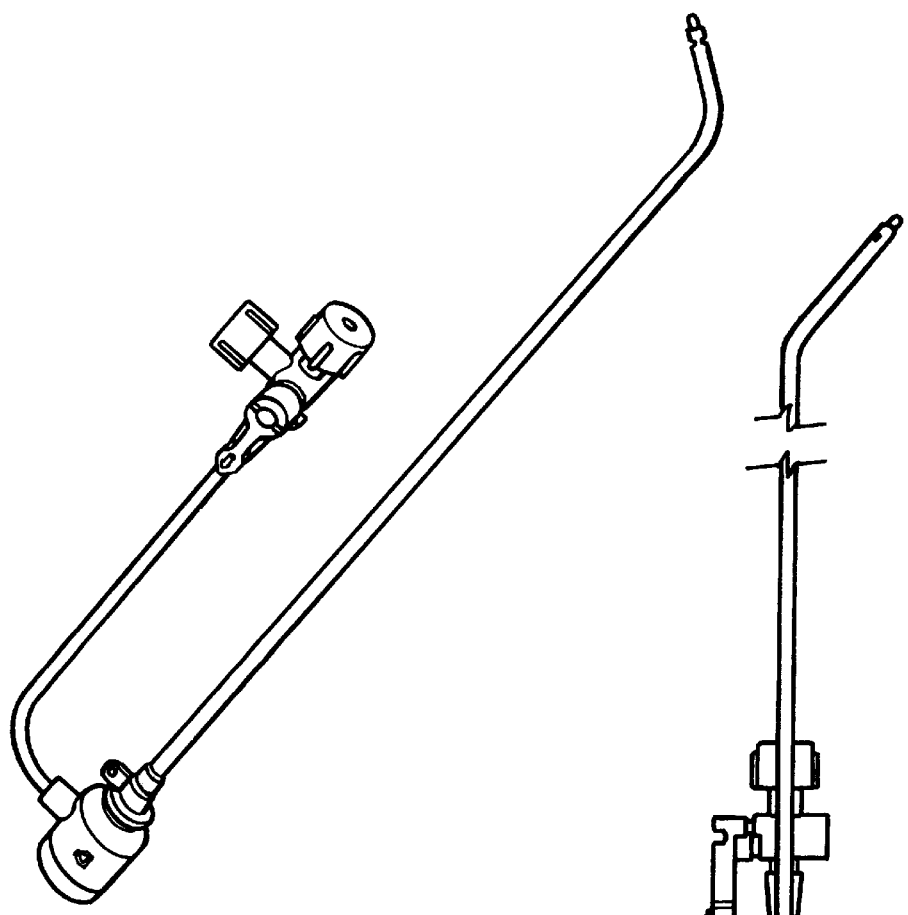
FIG. 15A is a first view of the outer guiding introducer for use in the left atrium as part of an alternative guiding introducer system to be used in combination with the inner guiding introducer of FIGS. 14A and 14B to produce the tracks shown in FIGS. 3C and 3D defined as tracks 3 and 4, wherein the side port, which is attached to the proximal end of the guiding introducer, is directed to the left of the outer guiding introducer, but generally in the same plane thereof.
FIG. 15B is a second view of the outer guiding introducer for use in the left atrium as shown in FIG. 15A rotated 90° clockwise from the position of FIG. 15A such that the side port is directed behind the first section of the outer guiding introducer and also rotated approximately 40° downward and to the right about the distal tip of the guiding introducer.
Figure 15D:
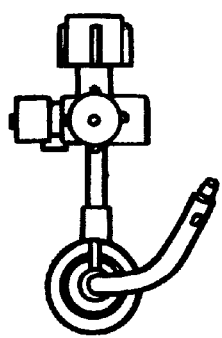
FIG. 15D is a fourth view from the top of the outer guiding introducer for use in the left atrium as shown in FIG. 15A with the proximal end rotated 90° upward from the position of FIG. 15B such that the side port is directed upward.
Figure 15C:
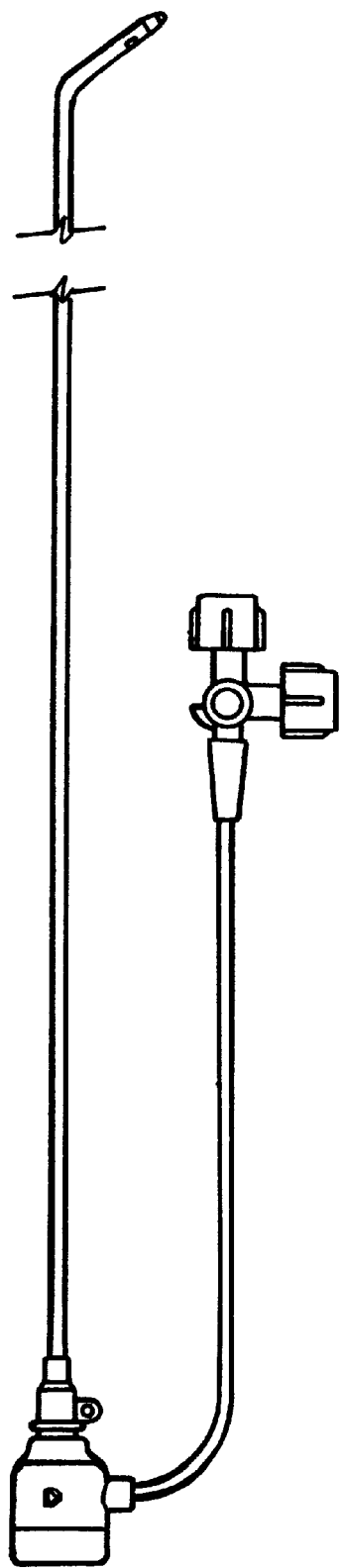
FIG. 15C is a third view of the outer guiding introducer for use in the left atrium as shown in FIG. 15A rotated 90° from the position of FIG. 15B such that the side port is directed to the right of the outer guiding introducer, but generally in the same plane thereof.

The second outer guiding introducer for use in the left atrium, in combination with the second inner guiding introducer disclosed in FIGS. 14A and 14B, is comprised of a first, second and third section. See FIGS. 15A, 15B, 15C and 15D. (The position of the second outer guiding introducer as shown in FIG. 15A is first rotated about the axis of the first section 90° such that the side port tubing is directed behind the second outer guiding introducer and then rotated approximately 40° downward and to the right about the distal end to produce FIG. 15B. FIG. 15B is rotated approximately 90° about the axis of the first section such that the side port tubing is directed to the right to produce FIG. 15C. The position of the second outer guiding introducer as shown in FIG. 15B is rotated upward approximately 90° so the side port tubing is directed upward to produce FIG. 15D. These positions best disclose the shape of the second outer guiding introducer.) The first section is a conventional, generally elongated, hollow straight introducer section of sufficient length for introduction of the patient and for manipulation from the point of insertion to the specific desired location within the heart. Merged with the distal end of the first section of the guiding introducer is the second section which is comprised of a curved portion followed by a straight portion, wherein the curved portion curves to the right as shown in FIG. 15B with a radius of about 0.3 in. (0.7 cm.) to about 0.7 in. (1.8 cm.) and preferably from about 0.4 in. (1.0 cm.) to about 0.6 in. (1.5 cm.) with an arc of about 20° to about 60° and preferably from about 30° to about 50°. Merged with the distal end of the curved portion is the straight portion which is from about 0.1 in. (0.2 cm.) to about 0.5 in. (1.3 cm.) and preferably from about 0.2 in. (0.5 cm.) to about 0.3 in. (0.8 cm.) in length ending in the third section which is comprised of a curved portion followed by a straight portion. The curved portion of the third section curves to the right as shown in FIG. 15C with a radius of about 0.2 in. (0.5 cm.) to about 0.5 in. (1.3 cm.) and preferably from about 0.3 in. (0.8 cm.) to about 0.4 in. (1.0 cm.) with an arc of about 30° to about 70° and preferably about 40° to about 60°. The straight portion of the third section is from about 0.4 in. (1.0 cm.) to about 0.9 in. (2.3 cm.) in length, and preferably about 0.6 in. (1.6 cm.) to about 0.8 in. (2.0 cm.) in length ending in the distal tip of the second outer guiding introducer.

Figure 3C:
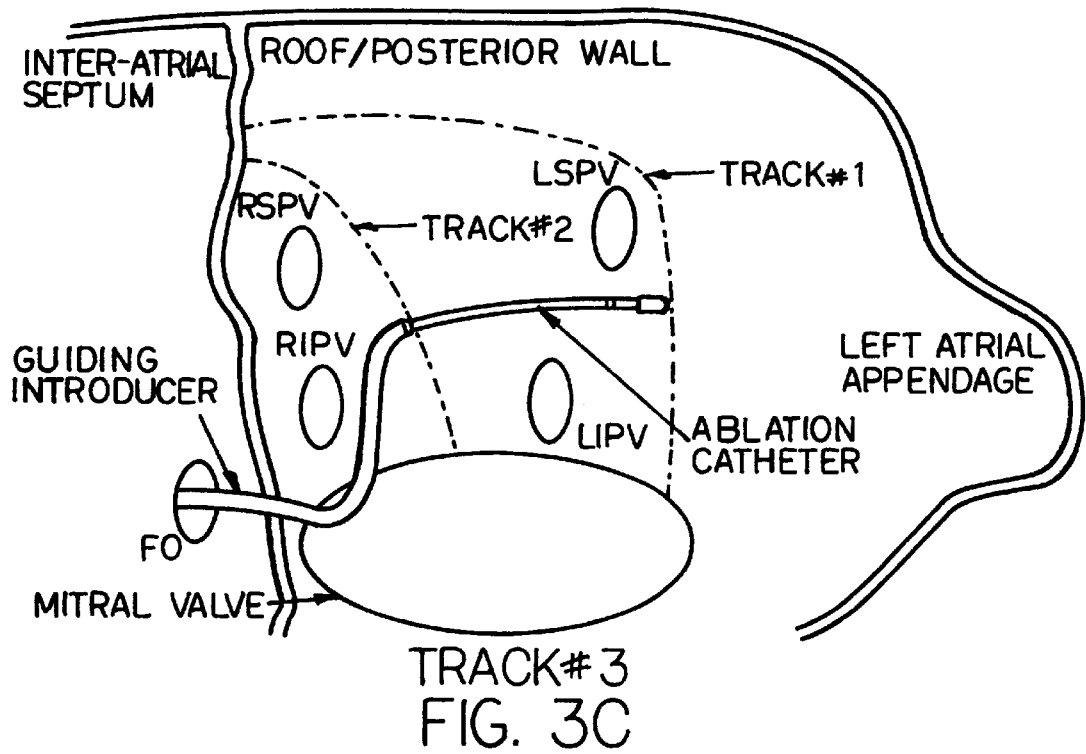
FIG. 3C is a schematic drawing of the left atrium showing the use of the third guiding introducer for the left atrium as shown in FIGS. 10A, B and C to produce track 3.
Figure 3D:
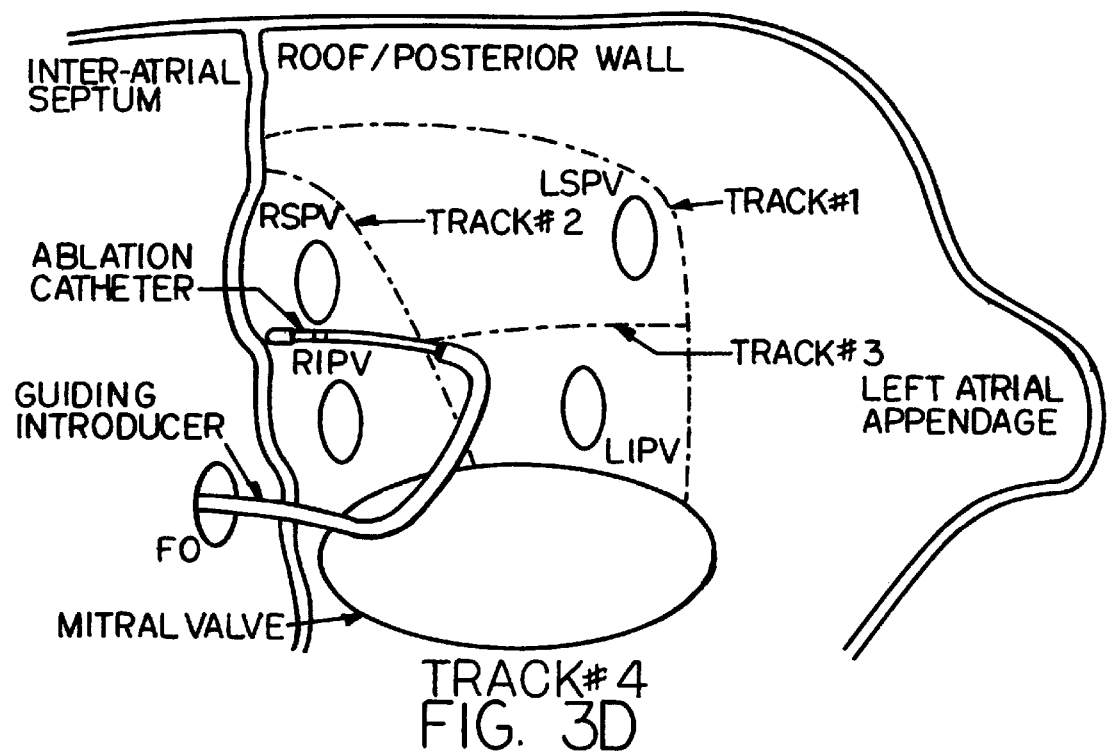
FIG. 3D is a schematic drawing of the left atrium showing the use of the fourth guiding introducer for the left atrium as shown in FIGS. 11A, B and C to produce track 4.
Figure 3E:
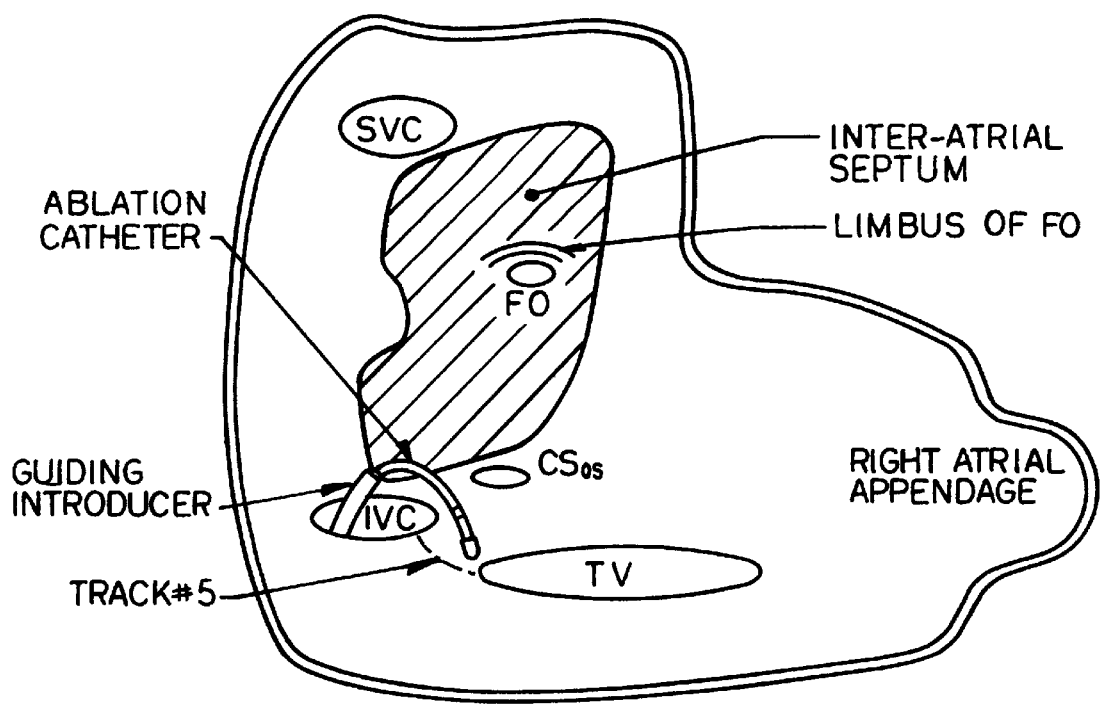
FIG. 3E is a schematic drawing of the right atrium showing the use of the first guiding introducer for the right atrium as shown in FIGS. 5A and B to produce track 5.
Figure 3F:
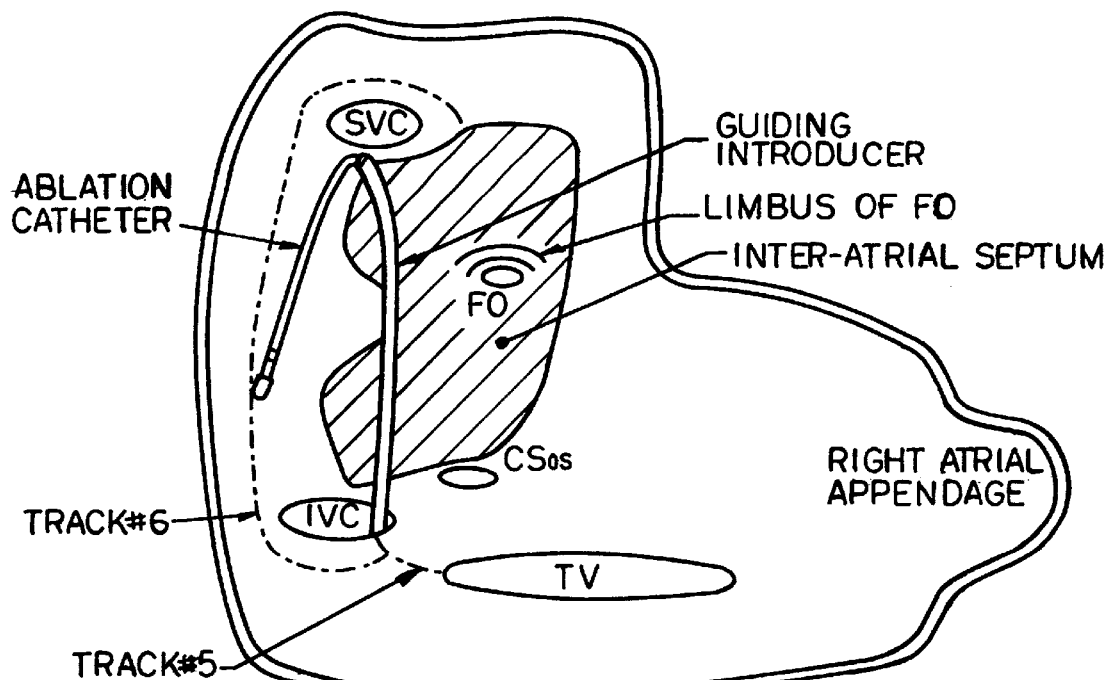
FIG. 3F is a schematic drawing of the right atrium showing the use of the second guiding introducer for the right atrium as shown in FIGS. 6A, B and C to produce track 6.
Figure 3G:
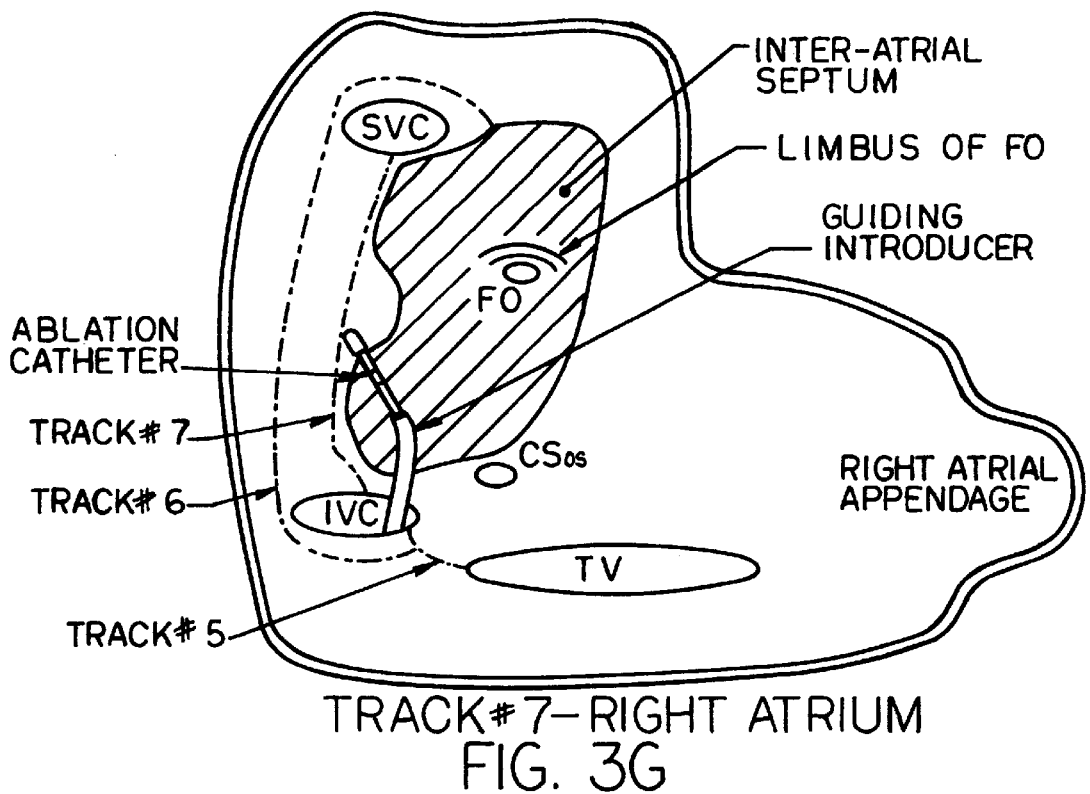
FIG. 3G is a schematic drawing of the right atrium showing the use of the third guiding introducer for the right atrium as shown in FIGS. 4A and B or an alternative use for the second guiding introducer for the right atrium as shown in FIGS. 6A, B and C to produce track 7.
Figure 3H:
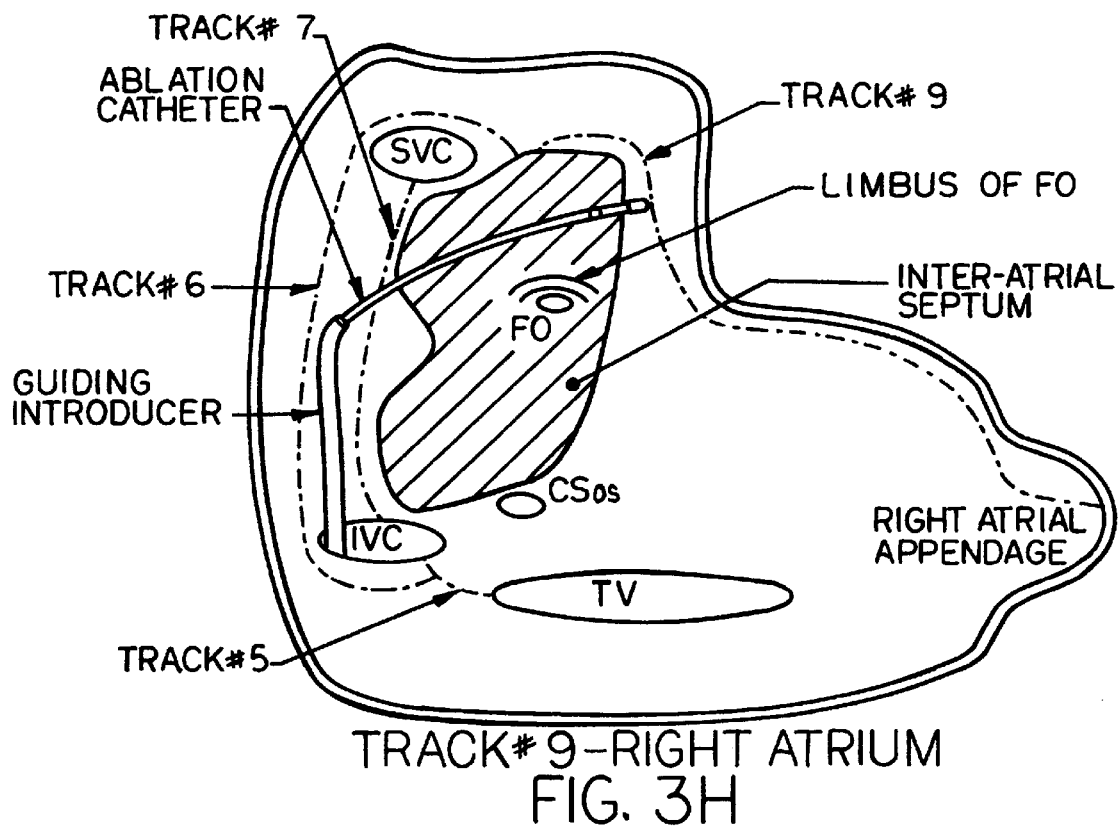
FIG. 3H is a schematic drawing of the right atrium showing the use of the third guiding introducer for the right atrium as shown in FIGS. 4A and B, or an alternative use of the second guiding introducer for the right atrium as shown in FIGS. 6A, B and C, to produce track 9.
Figure 31:
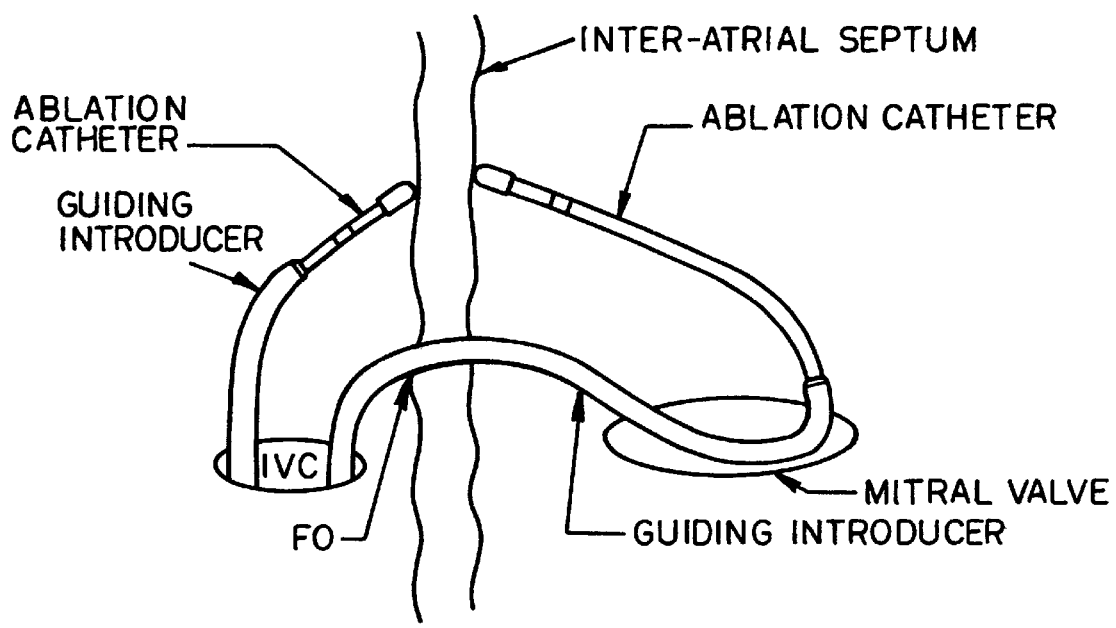
Figure 3J:
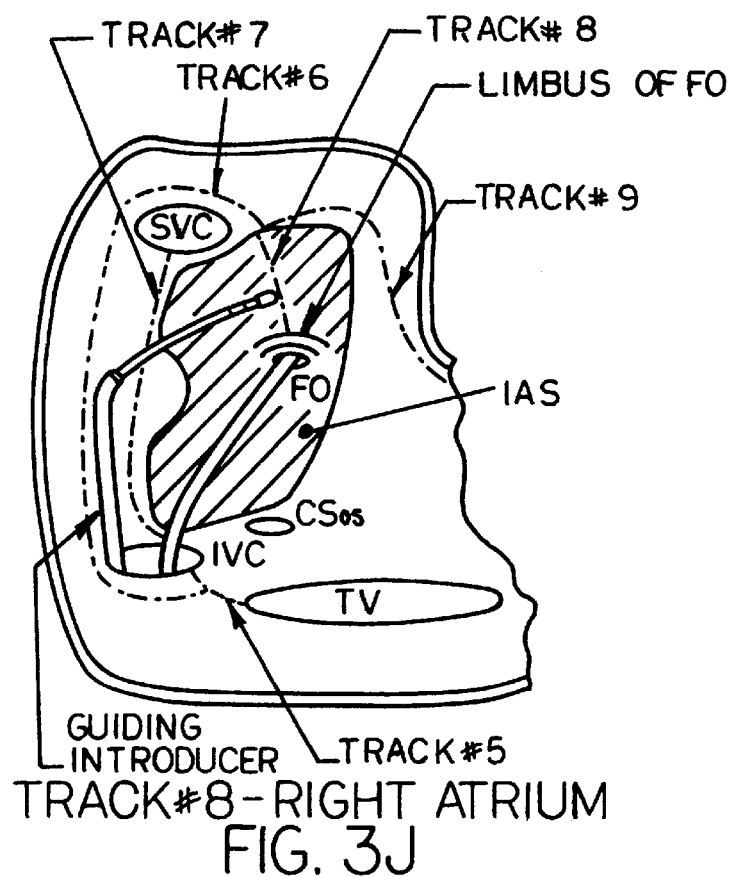
FIG. 3J is a schematic drawing of the right atrium showing the use of the guiding introducers in FIGS. 4A and B to produce track 8 in the right atrium.
Figure 3K:
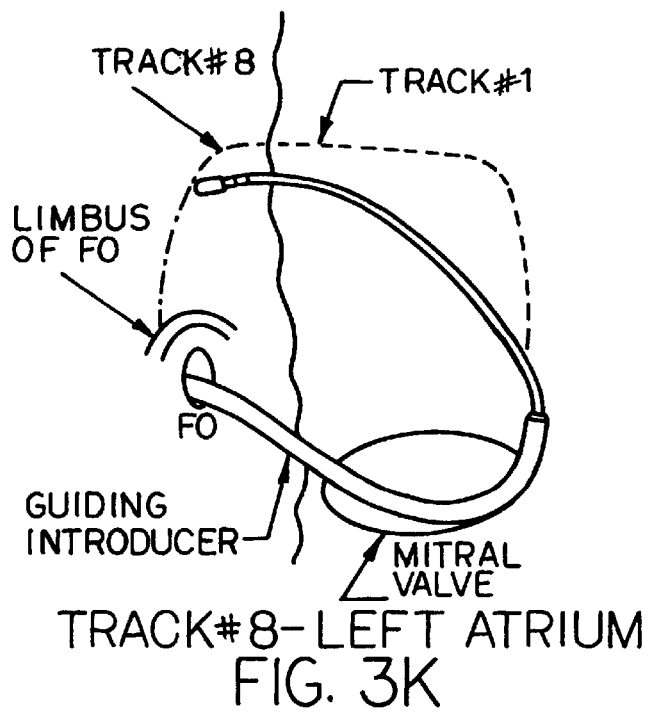
FIG. 3K is a schematic drawing of the left atrium showing the use of one of the guiding introducers used in FIG. 3I in the left atrium, as shown in FIGS. 7A, B and C, or an alternative use of the guiding introducer shown in FIGS. 8A and B, to produce track 8 in the left atrium.

By extending the distal tip of the second inner guiding introducer away from the distal tip of the second outer guiding introducer and by rotating the inner guiding introducer within the outer guiding introducer, a variety of shapes of the overall guiding introducer system are formed. These shapes permit ablation procedures for both tracks 3 and 4 of FIG. 2 as shown in FIGS. 3C and 3D to be performed, while, in addition, being adjustable to make modifications in those tracks as needed.

The combined effect of these four ablation tracks along with the ablation track along the interatrial septum will be the segregation of the left atrium into five discreet sections that do not directly communicate electrically with each other. Specifically, the small section of tissue around the left inferior pulmonary vein is isolated from the remaining portions of the left atrium. However, each of the other sections are able to undergo electrical activity or contraction moderated by the prevailing sinus rate. Based on experimental data and sensing operations, the number of ablation procedures may be reduced or increased.

While the preferred procedure in the left atrium creates five tracks, additional track may be necessary, especially if the heart is enlarged. Alternatively, fewer ablation procedures may be necessary under some circumstances depending on the needs of the particular patient.

Ablation procedures in the left atrium alone may be adequate to relieve the symptoms of atrial flutter. If so, no ablation procedures may be necessary in the right atrium. However, for the effective ablation of atrial fibrillation, ablation procedures should also occur in the right atrium.

In operation, a modified Seldinger technique is normally used for the insertion of the guiding introducers and ablation catheters into the body. Using this procedure, a small skin incision is made at the appropriate location to facilitate the catheter or dilator passage. Subcutaneous tissue is then dissected, followed by a puncture of the vessel with an appropriate needle with stylet positioned at a relatively shallow angle. The needle is then partially withdrawn and reinserted at a slightly different angle into the vessel making sure that the needle remains within the vessel. The soft flexible tip of an appropriate size guidewire is then inserted through, and a short distance beyond, the needle into the vessel. Firmly holding the guidewire in place, the needle is removed. The guidewire is then advanced through the vessel into the right femoral vein and through the inferior vena cava into the right atrium. (The preferred procedure uses the inferior approach to the right and left atria. Procedures for the retrograde and superior approach to the left atrium and superior approach to the right atrium can also be used. However, the shapes of the guiding introducers must be modified to adjust for the alternative approach.) With the guidewire in place, the dilator is then placed over the guidewire with the first guiding introducer, or guiding introducer system, to be used placed over the dilator. The dilator and the guiding introducer or guiding introducer system generally form an assembly to be advanced together along the guidewire into the inferior vena cava. After insertion of the assembly, the guidewire is then withdrawn.

The first guiding introducer for use in the right atrium is then passed over the guidewire to perform ablation and mapping procedures in the right atrium. The purpose of the ablation tracks in the right atrium is to prevent the formation of reentry circuits around the superior and inferior vena cava and the tricuspid valve, as well as to isolate the right atrial appendage. In the preferred procedure, the ablation tracks in the right atrium are first produced prior to production of the ablation track of the left atrium. See FIG. 1. While the order of ablation of the tracks in the right atrium is not critical, the preferred order of the tracks as shown in FIG. 1 is track 5, 6, 7, 9 and 8. Several passes along each track may be necessary to achieve complete ablation. Further, multi-electrode catheters may be used for ablation procedures. Sensing catheters can also be used in the right atrium to assure that complete ablation has been accomplished. Once it has been determined that adequate ablation has occurred, the last guiding introducer for the right atrium is removed to complete the process for the treatment of atrial arrhythmia in the right atrium.

After the procedures are completed in the right atrium, the last right side guiding introducer is removed and a Brockenbrough needle or trocar is then inserted through the lumen of the dilator to the right atrium to be used to create an opening through the interatrial septum, preferably at the fossa ovalis. (This procedure is used for insertion of the guiding introducers into the left atrium. The penetration of the interatrial septum will preferably be performed prior to completion of the right atrium procedures to permit the formation of a specific ablation track (See FIG. 2, track 8) in the left atrium at the same time the parallel track (FIG. 1, track 8) is formed in the right atrium. The entire assembly (dilator and Brockenbrough needle) passes through the vena cava into the right atrium so that the tip rests against the interatrial septum at the level of the fossa ovalis. The Brockenbrough needle is then advanced within the dilator to reach the fossa ovalis. After an opening is made through the interatrial septum, the needle, dilator and first guiding introducer for the left atrium or guiding introducer system are advanced into the left atrium. After the first guiding introducer or guiding introducers system for the left atrium is advanced through the interatrial septum into the left atrium, the Brockenbrough needle and dilator are removed leaving the first guiding introducer or guiding introducer system in the left atrium. The ablation catheter is then advanced through the lumen of the guiding introducer or the inner guiding introducer and is placed at the location within the left atrium which is created by the unique shape of the first guiding introducer or the guiding introducer system. The choice of the guiding introducer or guiding introducer system to be used will depend on the procedure chosen by the medical practitioner. Several passes across each preferred track may be necessary to effectively ablate the entire track. In the preferred procedure the four ablation guiding introducers are used in sequence one through four (see FIG. 2 and FIGS. 3A, 3B, 3C and 3D) to produce tracks 1, 2, 3 and 4 in order. Alternatively, the dual guiding introducer systems shown in FIGS. 12A, 12B, 13A, 13B, 14A, 14B, 15A, 15B, 15C and 15D can be used to produce some or all of tracks 1, 2, 3 and 4 in FIGS. 3A, 3B, 3C and 3D.

In a further alterative embodiment, the guiding introducer combination as shown in FIGS. 18A and 18B, 19A and 19B, 20A and 20B and 21A and 21B can be utilized to produce any of the ablation tracks shown in the left atrium as well as modifications to those tracks. The guiding introducer system utilized to form the combinations shown in FIGS. 18A and 18B, 19A and 19B, 20A and 20B and 21A and 21B include the inner guiding introducers shown in FIGS. 14A and 14B as a straight, uncurved guiding introducer utilized with the outer guiding introducers shown in FIGS. 16A, 16B and 17A and 17B. In addition, the system includes the use of the outer guiding introducer shown in 16A, 16B and 17A and 17B utilized with straight inner guiding introducers.

Obviously, modifications in the sequence of use of the guiding introducers can be made by the medical practitioners. After disconnecting the ablation source from the ablation catheter and connecting the catheter to the sensing equipment, a separate electrophysiology sensing catheter may be used with one or more of the shaped guiding introducers or guiding introducer systems to sense or map locations within the left atrium to determine whether an adequate ablation track has been created. As previously discussed, the procedure in the left atrium is designed to segregate the left atrium into five discreet segments that do not directly communicate with each other, but do communicate with the S.A. node. In addition, it is designed to segregate the tissue around the left interior pulmonary vein from all of the remaining tissue of the left atrium. By this procedure discreet pathways or corridors are created which will prevent or limit the formation of reentry circuits within the left atrium. While the location of specific tracks may change depending on the conditions of the individual heart, the general procedure as set forth above is the preferred procedure to achieve the results desired for the left atrium.

By choice of the desired guiding introducer or guiding introducer system in coordination with fluoroscopic viewing, the distal portion of the appropriate guiding introducer or introducers can be manipulated to direct the mapping and/or ablation catheter which is placed within the lumen of the guiding introducer, or the inner guiding introducer where dual guiding introducers are used, to a specific location within the left or right atrium. In addition, by providing sufficient rigidity and support, as the guiding introducer or introducers are held in place by the various anatomical structures of the heart, as well as the vascular surfaces, the distal end of the guiding introducer or introducers can be maintained at that fixed location or surface position of the endocardial structure to permit the appropriate ablation procedure. The precise location of the ablation catheter is important as there will be no dilution of the energy delivered due to the unfocused energy being dissipated over the entire cardiac chamber and lost in the circulating blood by a constantly moving tip of the ablating catheter. This permits a significantly reduced amount of energy to be applied during the ablation procedure. Further, time used to perform the procedure is significantly reduced over procedures where no guiding introducer is used. In addition, by this ablation procedure the same types of destruction of the discrete tracks can be achieved as have been accomplished, for example, in surgical applications such as by use of the "Maze" procedure, the corridor procedure and other such surgical procedures.

Pharmacological treatments may be used in combination with ablation procedures to relieve the atrial arrhythmia.

It will be apparent from the foregoing that while particular forms of the invention have been illustrated and described, various modifications can be made without departing from the spirit and scope of the invention. Accordingly, it is not intended that this invention be limited except as by the appended claims.

We claim:

1. A guiding introducer system adapted to conform to a heart, comprising a combination of an inner guiding introducer introduced within a lumen of an outer guiding introducer, wherein the combination of the inner and the outer guiding introducer forms an overall curved shape when a distal portion of the inner guiding introducer is extended from a distal end of the outer guiding introducer, wherein the shape of the combination of the inner and outer guiding introducer comprises an elongated section adapted to extend from an entry point of a patient to a location in the patient's inferior vena cava or right atrium, a left atrium section attached at a distal end of the elongated section and adapted to extend from the elongated section to a location in a left atrium of the heart and a trajectory section attached at a distal end of the left atrium section and adapted to extend from the left atrium section to a desired trajectory toward a wall of the left atrium of the patient's heart.

2. The guiding introducer system of claim 1 wherein the elongated section is a generally elongated straight section.

3. The guiding introducer system of claim 1 wherein the left atrium section comprises a curved portion, wherein the curved portion comprises an arc with a radius and a curvature, wherein the radius of the arc is from about 1.5 in. (3.8 cm.) to about 4 in. (10.2 cm.) and the curvature of the arc is from about 45° to 90°.

4. The guiding introducer system of claim 3 wherein the left atrium section further comprises a straight section attached to the curved portion, wherein the length of the straight section is up to about 8.0 in. (20.3 cm.).

5. The guiding introducer system of claim 3 wherein the left atrium section further comprises a straight section attached to the curved portion, wherein the length of the straight section is up to about 3.0 in.

6. The guiding introducer system of claim 1 wherein the trajectory section comprises a curved portion, wherein the curved portion comprises an arc with a radius and a curvature, wherein the radius of the arc is from about 0.1 in. (0.2 cm.) to about 1.0 in. (2.6 cm.) and the curvature of the arc is from about 60° to about 150°.

7. The guiding introducer system of claim 6 wherein the trajectory section further comprises a straight section attached to the curved portion, wherein the length of the straight section is at least about 0.25 in. (0.6 cm.).

8. The guiding introducer system of claim 1 wherein the left atrium section comprises a curved portion, wherein the curved portion comprises an arc with a radius and a curvature, wherein the radius of the arc is from about 0.6 in. (2.5 cm.) to about 3.0 in. (7.7 cm.) and the curvature of the arc is from about 60° to 130°.

9. The guiding introducer system of claim 8 wherein the left atrium section further comprises a straight section attached to the curved portion, wherein the length of the straight section is up to about 8.0 in. (20.3 cm.).

10. The guiding introducer system of claim 8 wherein the left atrium section further comprises a straight section, wherein the length of the straight section is up to about 3.0 in. (7.6 cm.).

11. The guiding introducer system of claim 1 wherein the outer guiding introducer comprises a precurved shape wherein the shape comprises a second elongated section and a second left atrium section secured to the second elongated section.

12. The guiding introducer system of claim 11 further comprising a second trajectory section secured to the second left atrium section.

13. The guiding introducer system of claim 11 wherein the second elongated section is a generally elongated straight section.

14. The guiding introducer system of claim 11 wherein the second left atrium section comprises a curved portion with an arc with a radius and a curvature, wherein the radius of the arc is from about 0.3 in. (0.7 cm.) to about 1.2 in. (3.1 cm.) and the curvature of the arc is from about 180 to about 300° degrees.

15. The guiding introducer system of claim 12 wherein the second trajectory section comprises a straight portion which is up to about 4.0 in. (10.1 cm.).

16. The guiding introducer system of claim 12 wherein the second trajectory section comprises a straight portion less than about 0.5 in. (1.3 cm.) in length.

17. The guiding introducer system of claim 11 wherein the second left atrium section comprises a curved portion with an arc with a radius and a curvature, wherein the radius of the arc is from about 0.5 in. (1.2 cm.) to about 2.0 in.(3.1 cm.) and the curvature is from about 90° to about 180° degrees.

18. The guiding introducer system of claim 12 wherein the second trajectory section comprises a straight portion which is up to about 4.0 in. (10.1 cm.) in length.

19. The guiding introducer system of claim 12 wherein the second trajectory section comprises a straight portion less than 0.5 in. (1.3 cm.) in length.

20. The guiding introducer system of claim 1 wherein the elongated section, left atrium section and trajectory section are substantially contiguous.

21. The guiding introducer system of claim 1 wherein the elongated section, the left atrium section and the trajectory section are substantially adapted to extend from the entry point of the patient to the desired trajectory in the left atrium of the patient.

* * * * *